United States Patent
Houser

(10) Patent No.: US 7,150,721 B2
(45) Date of Patent: Dec. 19, 2006

(54) KNEE BRACE WITH DYNAMIC COUNTERFORCE

(75) Inventor: Guy M. Houser, Bainbridge Island, WA (US)

(73) Assignee: Thuasne, Levallois Perret (FR)

( * ) Notice: Subject to any disclaimer, the term of this patent is extended or adjusted under 35 U.S.C. 154(b) by 135 days.

(21) Appl. No.: 10/880,228

(22) Filed: Jun. 29, 2004

(65) Prior Publication Data

US 2004/0267177 A1 Dec. 30, 2004

Related U.S. Application Data

(60) Provisional application No. 60/484,050, filed on Jun. 30, 2003.

(51) Int. Cl.
A61F 5/00 (2006.01)
(52) U.S. Cl. .............................. 602/16; 602/5; 602/26; 602/23
(58) Field of Classification Search .................... 602/5, 602/16, 20, 23, 26, 62
See application file for complete search history.

(56) References Cited

U.S. PATENT DOCUMENTS

| | | |
|---|---|---|
| 2,573,596 A | 10/1951 | Young |
| 2,573,866 A | 11/1951 | Murphy |
| 3,528,412 A | 9/1970 | McDavid |
| 3,799,158 A | 3/1974 | Gardner |
| 4,323,059 A | 4/1982 | Rambert |
| 4,337,764 A | 7/1982 | Lerman |
| 4,407,276 A | 10/1983 | Bledsoe |
| 4,489,718 A | 12/1984 | Martin |
| 4,493,316 A | 1/1985 | Reed et al. |
| 4,502,472 A | 3/1985 | Pansiera |
| 4,520,802 A | 6/1985 | Mercer et al. |
| 4,599,998 A | 7/1986 | Castillo |
| 4,620,532 A | 11/1986 | Houswerth |
| 4,633,867 A | 1/1987 | Kausek |
| 4,697,583 A | 10/1987 | Mason |
| 4,802,467 A | 2/1989 | Pansiera |
| 4,865,024 A | 9/1989 | Hensley et al. |
| 4,881,299 A | 11/1989 | Young |
| 4,886,054 A | 12/1989 | Castillo et al. |
| 4,928,676 A | 5/1990 | Pansiera |
| 4,938,207 A | 7/1990 | Vargo |

(Continued)

FOREIGN PATENT DOCUMENTS

EP 0641551 3/1995

(Continued)

OTHER PUBLICATIONS

EBI A Biomet Company, "The Edge PCL Opposition Knee Brace," Online. Internet. May 13, 2002. Available http://www.ebimedical.com/products/sportsmed/knee/opposition.html (1 pg).

(Continued)

*Primary Examiner*—Henry Bennett
*Assistant Examiner*—Shumaya B. Ali
(74) *Attorney, Agent, or Firm*—www.perkinscoie,com

(57) ABSTRACT

Braces for applying dynamic forces and methods for applying dynamic forces on limbs are disclosed herein. In one embodiment, a brace has an upper frame, a lower frame, a hinge coupling the upper frame to the lower frame, a hydraulic pump, and a bladder. The upper frame is moveable relative to the lower frame. The hydraulic pump is coupled to the hinge, the upper frame or the lower frame. The hydraulic pump generates a fluid flow that flows into and expands the bladder. The bladder is positioned to apply a force to the limb as it expands.

19 Claims, 18 Drawing Sheets

U.S. PATENT DOCUMENTS

| | | | |
|---|---|---|---|
| 4,961,416 A | 10/1990 | Moore | |
| 4,986,264 A | 1/1991 | Miller | |
| 5,000,170 A | 3/1991 | Young | |
| 5,018,514 A | 5/1991 | Grood | |
| 5,038,765 A | 8/1991 | Young et al. | |
| 5,039,247 A | 8/1991 | Young et al. | |
| 5,060,640 A | 10/1991 | Rasmusson | |
| 5,230,697 A | 7/1993 | Castillo | |
| 5,259,832 A | 11/1993 | Townsend | |
| 5,288,287 A | 2/1994 | Castillo | |
| 5,356,370 A | 10/1994 | Fleming | |
| 5,399,154 A | 3/1995 | Kipnis et al. | |
| 5,419,754 A | 5/1995 | Hutchins | |
| 5,437,611 A | 8/1995 | Stern | |
| 5,443,444 A | 8/1995 | Pruyssers | |
| 5,460,599 A | 10/1995 | Davis | |
| 5,462,517 A | 10/1995 | Mann | |
| 5,472,412 A | 12/1995 | Knoth | |
| 5,507,719 A | 4/1996 | Freeman | |
| 5,586,970 A | 12/1996 | Morris | |
| 5,641,322 A | 6/1997 | Silver et al. | |
| 5,643,185 A | 7/1997 | Watson | |
| 5,658,241 A | 8/1997 | Deharde et al. | |
| 5,662,596 A | 9/1997 | Young | |
| 5,749,840 A | 5/1998 | Mitchell et al. | |
| 5,772,618 A | 6/1998 | Mason et al. | |
| 5,776,086 A | 7/1998 | Pansiera | |
| 5,782,785 A | 7/1998 | Herzberg | |
| 5,792,084 A | 8/1998 | Wilson | |
| 5,865,166 A * | 2/1999 | Fitzpatrick et al. | 128/117.1 |
| 5,885,235 A | 3/1999 | Opahle et al. | |
| 5,891,061 A | 4/1999 | Kaiser | |
| 6,074,355 A | 6/2000 | Bartlett | |
| RE37,297 E | 7/2001 | Smith | |
| 6,314,612 B1 | 11/2001 | Rennecke et al. | |
| 6,387,066 B1 | 5/2002 | Whiteside | |
| 6,390,998 B1 | 5/2002 | Doyle | |
| 6,402,711 B1 | 6/2002 | Nauert | |
| 6,402,713 B1 | 6/2002 | Doyle | |
| 6,413,232 B1 | 7/2002 | Townsend et al. | |
| 6,527,733 B1 | 3/2003 | Ceriani et al. | |
| 6,540,707 B1 | 4/2003 | Stark et al. | |
| 6,540,709 B1 | 4/2003 | Smits | |
| 6,666,837 B1 | 12/2003 | Weihermuller | |
| 6,740,054 B1 | 5/2004 | Stearns | |
| 6,746,413 B1 | 6/2004 | Reinecke et al. | |
| 6,752,775 B1 | 6/2004 | Seligman et al. | |
| 6,875,187 B1 | 4/2005 | Castillo | |
| 6,878,126 B1 | 4/2005 | Nelson et al. | |
| 6,908,488 B1 | 6/2005 | Passivaara et al. | |
| 6,971,996 B1 * | 12/2005 | Houser | 602/16 |

FOREIGN PATENT DOCUMENTS

| | | |
|---|---|---|
| EP | 0684026 | 11/1995 |
| EP | 1088534 | 4/2001 |
| WO | WO-92/03110 | 3/1992 |
| WO | WO-99/20212 | 4/1999 |
| WO | WO-01/66049 | 9/2001 |
| WO | WO-02/02035 | 1/2002 |

OTHER PUBLICATIONS

Generation II USA Inc., "PS-1 Patella Stabilizer," Online. Internet. May 13, 2002. Available http://www.gen2.com/PS-1/PS-1.asp?page=pysician (2 pgs).

Generation II USA Inc., "OA Braces Unloader Bi-ComPF," Online. Internet. May 13, 2002. Available http://www.gen2.com/Bi-Com/Bi-com.asp?page=physician (2 pgs).

Generation II USA Inc., "Ligament Braces Extreme Select," Online. Internet. May 13, 2002. Available http://www.gen2.com/LigBrace/ExtremeSelect.asp?page=pysician (1 pg).

Comfy Splints. Elbow and Knee Splints. Online . Internet. May 13, 2002. Available http://www.comfyspints.com/elbow-knee.htm (2 pgs).

Innovation Sports, "XCL" Online. Internet. May 13, 2002. Available http://www.isports.com/xcl.html (2 pgs).

Knapp Hinged Knee Orthosis. Online. Internet. May 13, 2002. Available http://www.hely-weber.com/knapphinged.htm (2 pgs).

Innovation Sports—Medical Experts, "ACL Cable System," Online. Internet. May 13, 2002. Available http://www.isports.com/medi.htm (1 pg).

Dj Orthopedics, Inc., "TROM," Online. Internet. May 13, 2002. Available http://www.donjoy.com/products/feattrom.html (1 pg).

International Search Report and Written Opinion of PCT Application No. US04/21094, dated Nov. 11, 2004—corresponding to the present application.

* cited by examiner

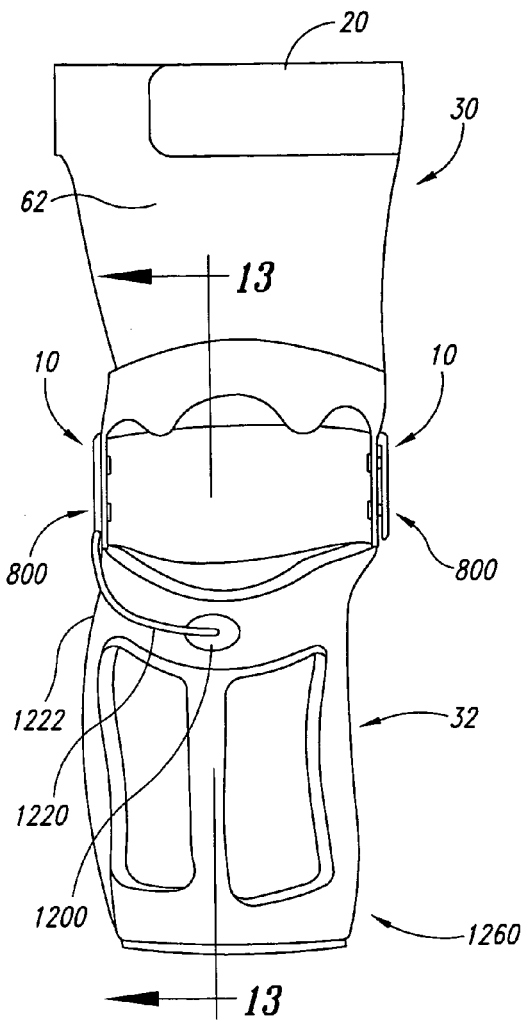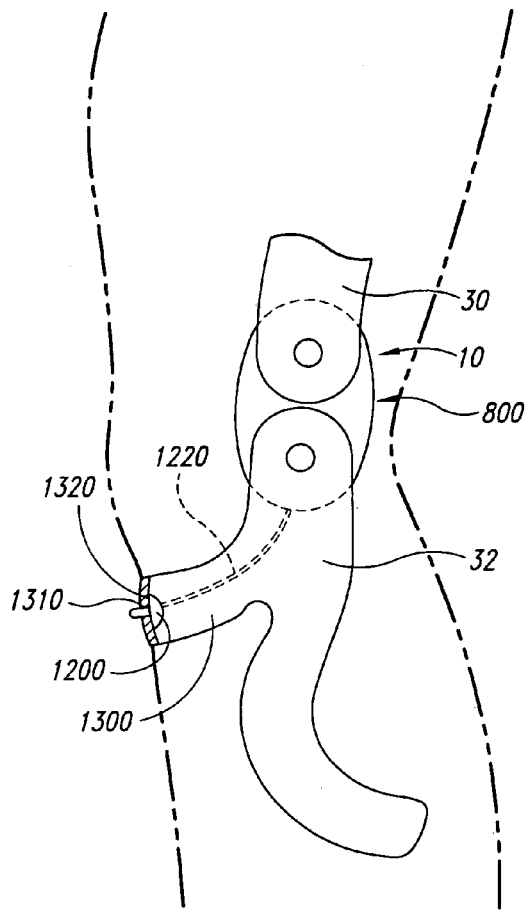
*Fig. 12*          *Fig. 13*
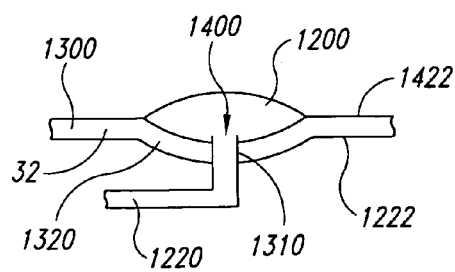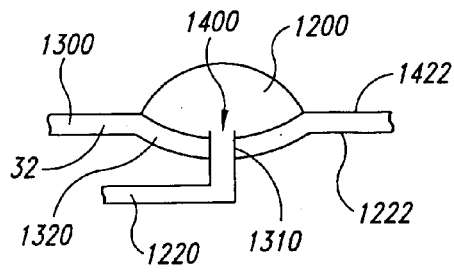
*Fig. 14A*          *Fig. 14B*

KNEE BRACE WITH DYNAMIC COUNTERFORCE

RELATED APPLICATIONS

This application claims the benefit of provisional U.S. Patent Application Ser. No. 60/484,050, filed Jun. 30, 2003, which is hereby incorporated by reference in its entirety.

TECHNICAL FIELD

The present invention relates to knee braces with dynamic counterforces.

BACKGROUND

Investigations have shown that the anterior cruciate ligament (ACL) is rarely lax and experiences the greatest tension at full-extension. If an ACL is torn, or if for some other reason the knee encounters an anterior instability, the knee requires support at full-extension. Conventional knee braces provide support to the tibial condyles by applying a force with a static strap or a rigid frame.

Application of a force with a static strap or a rigid frame has several disadvantages. First, the static strap and rigid frame spread the force over a relatively large amount of generally soft tissue. Second, if the static strap or rigid frame were to produce a sustained, concentrated force on the tibial tuberosity, it would be extremely uncomfortable for the wearer over time. Consequently, the wearer would likely loosen the straps and thereby eliminate the necessary supportive force.

Moreover, studies have shown that the posterior cruciate ligament (PCL) prevents posterior displacement of the tibia on the femur and prevents hyperextension at the knee joint. These studies also indicate that the PCL is taut at full-extension, becomes progressively more lax until 30 degrees of flexion, and thereafter becomes increasingly more tense until it reaches a maximum tension at 130 degrees of flexion. When the PCL is torn, a posterior instability can result that produces a greater susceptibility to further weaken or tear the PCL due to hyperextension.

Typical knee braces attempt to prevent hyperextension through range of motion stops. It is difficult, however, to prevent hyperextension using range of motion stops because of the soft tissue in and around the knee. The range of motion stops stop the rigid frame from rotating, but the soft tissue in the knee can give, allowing hyperextension.

SUMMARY

The present invention is directed toward braces for applying dynamic forces and methods for applying dynamic forces on limbs. In one embodiment of the invention, a brace has an upper frame, a lower frame, a hinge coupling the upper frame to the lower frame, a hydraulic pump, and a bladder. The upper frame is moveable relative to the lower frame. The hydraulic pump is coupled to the hinge, the upper frame, or the lower frame. The hydraulic pump also generates a fluid flow that flows into and expands the bladder. The bladder is positioned to apply a force to the limb as it expands.

An embodiment for applying the dynamic force on the limb includes placing the bladder proximate to the limb and filling the bladder at least partially with the fluid to expand the bladder. The method further includes exerting the force on the limb as the bladder expands and draining the bladder at least partially to at least partially release the force.

BRIEF DESCRIPTION OF THE DRAWINGS

FIG. 12 is a front view of a knee brace having a bladder to exert a force on the tibial tuberosity in accordance with one embodiment of the invention.

FIG. 13 is a partial cross-sectional view taken substantially along line 13—13 of FIG. 12.

FIGS. 14A and 14B are partial cross-sectional views illustrating the bladder empty and filled with fluid.

DETAILED DESCRIPTION

The following disclosure describes several embodiments of braces with dynamic counterforces and methods for applying counterforces to limbs. Many specific details of certain embodiments of the invention are set forth in the following description and in FIGS. 1–18 to provide a thorough understanding of such embodiments. One skilled in the art, however, will understand that the invention may have additional embodiments or that the invention may be practiced without several of the details described in the following description. For example, even though many embodiments of the braces with dynamic counterforces are described with reference to a knee brace, they can also be used in elbow braces or other braces.

Figure 1:
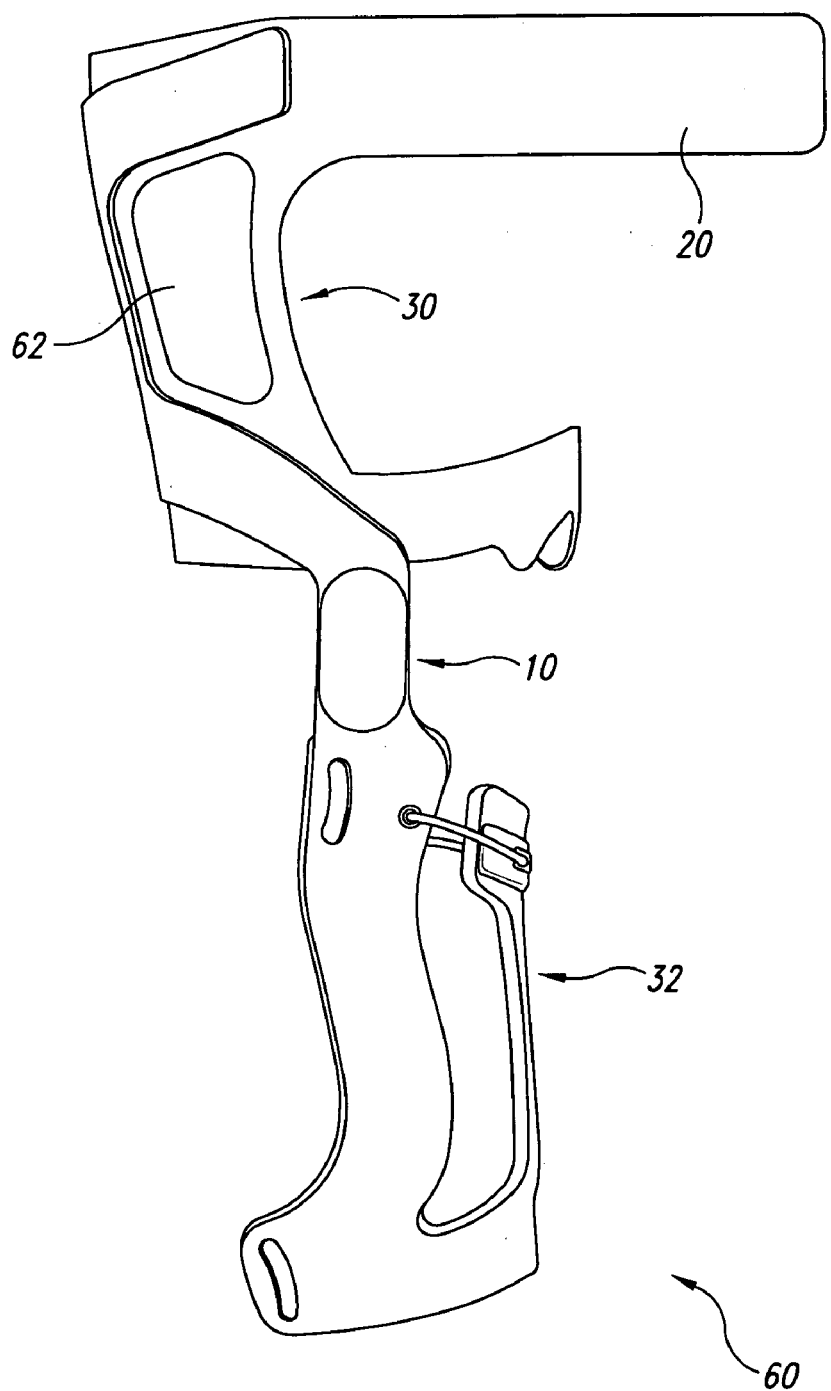
FIG. 1 is a side view of a knee brace with a hinge in accordance with one embodiment of the invention.

FIG. 1 is a side view of a knee brace 60 including an upper frame 30, a lower frame 32, and hinges 10 connecting the upper frame 30 to the lower frame 32. The upper frame 30 can include at least one strap 20 to wrap around the quadriceps or hamstring, and the lower frame 32 can also include one or more straps. In other embodiments, the upper and lower frames 30 and 32 can have different configurations and include different configurations of straps. For example, the knee brace 60 can also include a flexible, elastic sleeve 62 coupled either directly or indirectly to the upper and lower frames 30 and 32.

Figure 2:
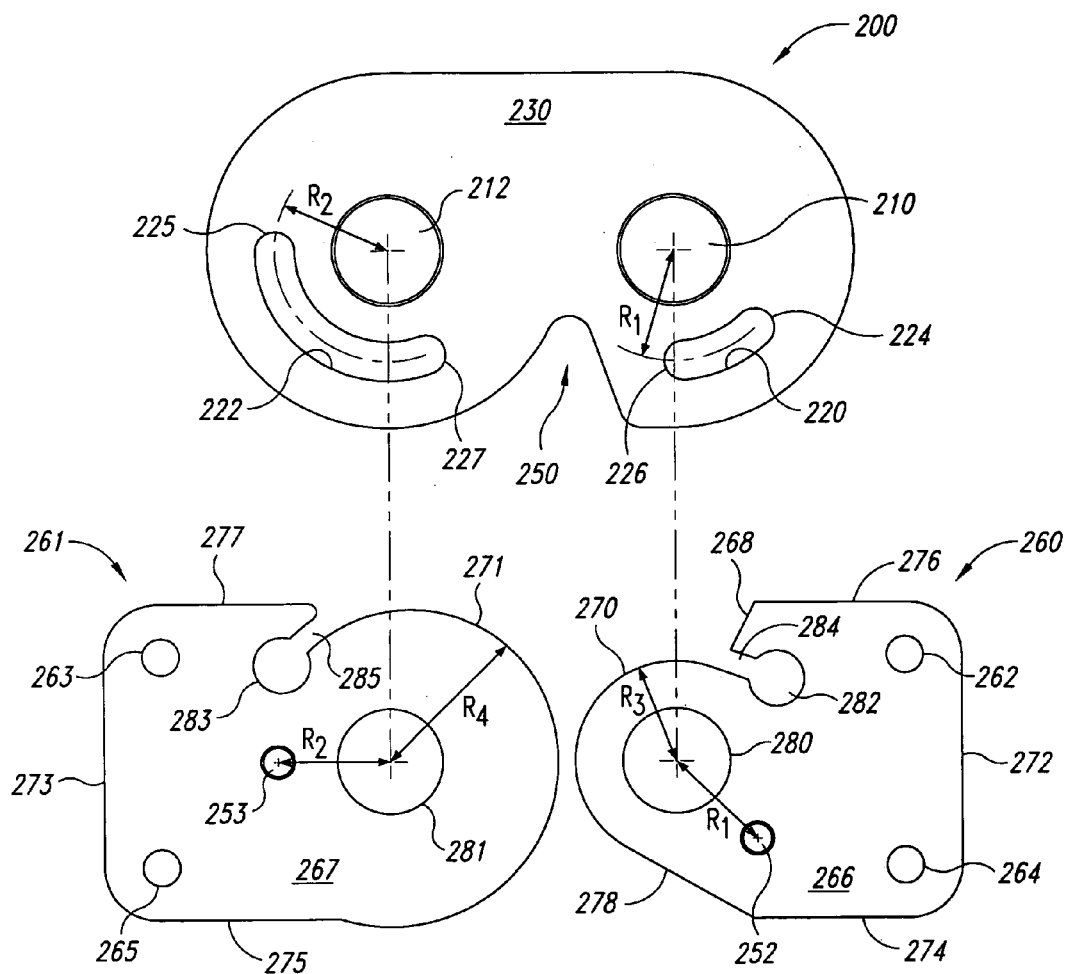
FIG. 2 is an exploded view of a plate, a first hinge member, and a second hinge member of the hinge of FIG. 1.
Figure 3A:
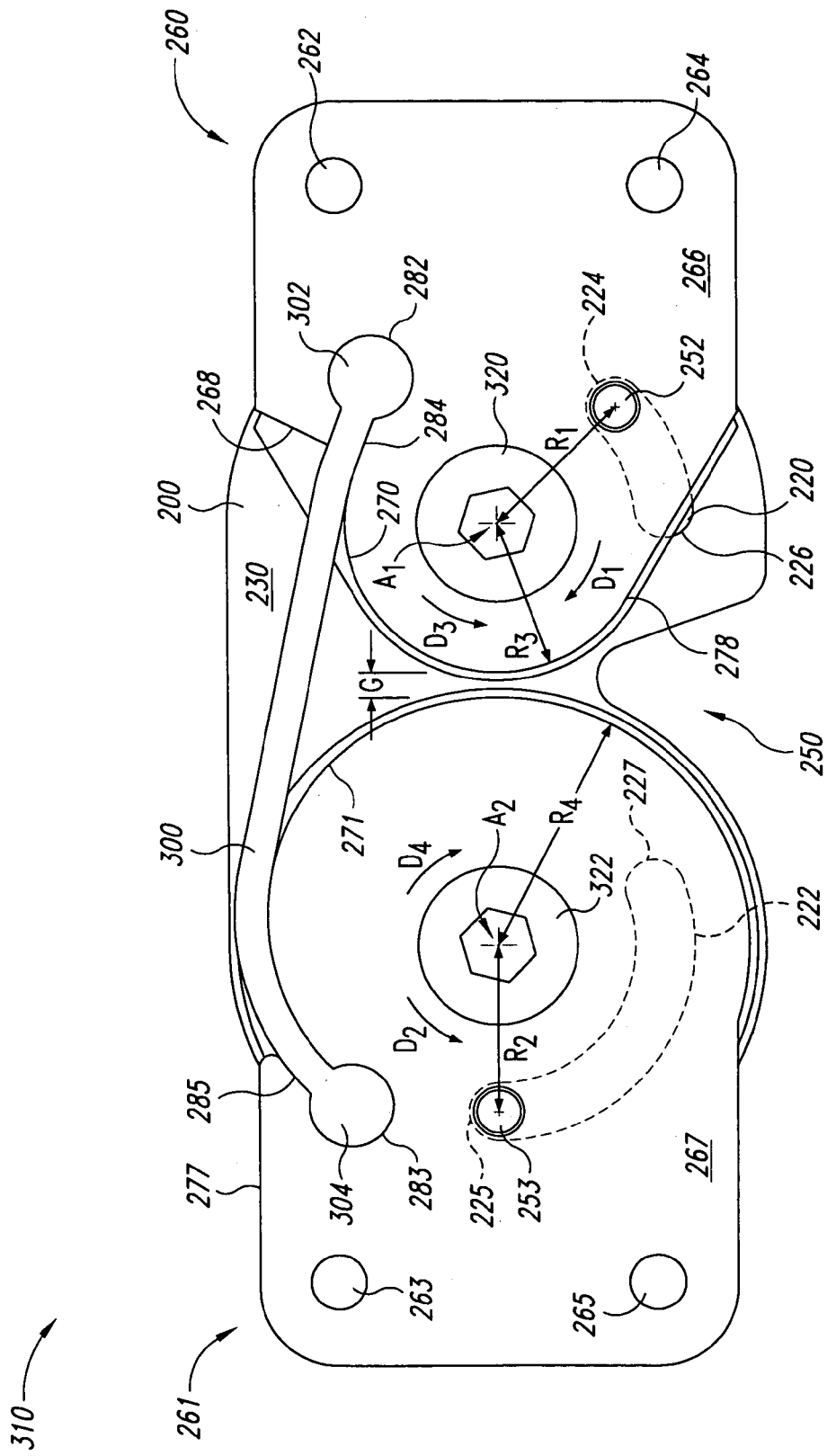
FIG. 3A is a top plan view of an assembly including a resilient member with the plate, the first hinge member, and the second hinge member of FIG. 2.

FIG. 2 is an exploded view and FIG. 3A is a top plan view of one embodiment of the hinge 10. In this embodiment, the hinge 10 includes a back plate 200, a first hinge member 260, and a second hinge member 261. The first hinge member 260 rotatably mounts to the back plate 200 and is configured to attach to the upper frame 30 (FIG. 1) to permit the upper frame 30 to pivot relative to the back plate 200. The second hinge member 261 also rotatably mounts to the back plate 200 and is configured to attach to the lower frame 32 (FIG. 1) to permit the lower frame 32 to pivot relative to the back plate 200 independently of the upper frame 30. Accordingly, the upper and lower frames 30 and 32 pivot independently about two different axes of rotation.

Referring to FIG. 2, the first hinge member 260 is a generally flat plate with a front surface 266 and a back surface (not shown) opposite the front surface 266. Between the front surface 266 and the back surface are a top edge 276, a bottom edge 274 and a side edge 272 configured for attachment to a portion of the upper frame 30. For example, the first hinge member 260 can include two apertures 262 and 264 proximate to the side edge 272 for receiving fasteners (not shown) to connect the upper frame 30 to the first hinge member 260. The second hinge member 261, similarly, has a front surface 267 and a back surface (not shown) opposite the front surface 267. Between the front surface 267 and the back surface are a top edge 277, a bottom edge 275 and a side edge 273 configured for attachment to a portion of the lower frame 32. The second hinge member 261 can also include two apertures 263 and 265 proximate to the side edge 273 for receiving fasteners (not shown) to connect the lower frame 32 to the second hinge member 261. In additional embodiments, the first hinge member 260 can be an integral portion of the upper frame 30 and the second hinge member 261 can be an integral portion of the lower frame 32. The first and second hinge members 260 and 261 can have different configurations in other embodiments.

Referring to FIGS. 2 and 3A together, the first hinge member 260 is pivotally connected to the back plate 200 by a fastener 320. The first hinge member 260 rotates relative to the back plate 200 about a first axis of rotation $A_1$ (FIG. 3A). The first hinge member 260 has a pin 252 that projects from the front surface 266 and the back surface. In additional embodiments, the pin 252 can have a different configuration or shape. For example, the pin 252 can extend or project from either the front surface 266 or the back surface. The portion of the pin 252 projecting from the back surface is received within an annular slot 220 in the back plate 200. The annular slot 220 is accordingly centered about the first axis of rotation $A_1$ with a centerline at a radius $R_1$ corresponding to the distance from the first axis of rotation $A_1$ to the pin 252. Accordingly, as the first hinge member 260 rotates relative to the back plate 200 about the first axis of rotation $A_1$, the pin 252 slides in the annular slot 220. A first endpoint 224 and a second endpoint 226 of the slot 220 define the maximum range of motion for the first hinge member 260. Accordingly, the length of the slot 220 determines the pivoting range of the first hinge member 260 relative to the back plate 200. In additional embodiments, the slot 220 can have different lengths to change the pivoting range of the first hinge member 260. In other embodiments, the position of the slot 220 and the pin 252 can be different, such as the slot 220 can be in the first hinge member 260 and the pin 252 can be attached to the back plate 200.

The second hinge member 261 is pivotally connected to the back plate 200 by a fastener 322. The second hinge member 261 rotates relative to the back plate 200 about a second axis of rotation $A_2$ (FIG. 3A). The second hinge member 261 has a pin 253 that projects from the front surface 267 and the back surface. In additional embodiments, the pin 253 can have a different configuration or shape. For example, the pin 253 can extend or project from either the front surface 267 or the back surface, or there can be two separate pins with one extending from each surface. The portion of the pin 253 projecting from the back surface is received within an annular slot 222 in the back plate 200. The annular slot 222 is accordingly centered about the second axis of rotation $A_2$ with a centerline at a radius $R_2$ corresponding to the distance from the second axis of rotation $A_2$ to the pin 253. As the second hinge member 261 rotates relative to the back plate 200 about the second axis of rotation $A_2$, the pin 253 slides in the annular slot 222. A first endpoint 225 and a second endpoint 227 of the slot 222 define the maximum range of motion for the second hinge member 261. The length of the slot 222 determines the pivoting range of the second hinge member 261 relative to the back plate 200. In additional embodiments, the slot 222 can have a different length to change the pivoting range of the second hinge member 261. In other embodiments, the position of the slot 222 and the pin 253 can be different, such as the slot 222 can be in the second hinge member 261 and the pin 253 can be attached to the back plate 200.

Referring to FIG. 3A, the curved edge 270 on the first hinge member 260 is spaced away from the curved edge 271 on the second hinge member by a gap G. Accordingly, the first hinge member 260 and the second hinge member 261 pivot independently about the two different axes of rotation $A_1$ and $A_2$. Because the hinge has two different and independent axes of rotation, it better simulates the natural motion of the knee joint. This is expected to mitigate the sliding of the knee brace down the leg and reduce the exertion of unnatural forces against the knee joint.

In the illustrated embodiment, the back plate 200 has a cutout portion 250.

The cutout portion 250 allows the first and second hinge members 260 and 261 to rotate through the full pivoting range without the upper and lower frames 30 and 32 (FIG. 1) striking the back plate 200.

In the illustrated embodiment, the first hinge member 260 and the second hinge member 261 are operatively coupled by a resilient member 300. The resilient member 300 has a first end 302 attached to the first hinge member 260 and a second end 304 attached to the second hinge member 261. The first end 302 is received within an aperture 282 in the first hinge member 260. A channel 284 connects the aperture 282 to an edge 268 and is sized to receive a portion of the resilient member 300. Similarly, the second end 304 of the resilient member 300 is received within an aperture 283 of the second hinge member 261. A channel 285 connects the aperture 283 to the edge 277 and is sized to receive a portion of the resilient member 300. The first end 302 and the second end 304 of the resilient member 300 are enlarged so that they are not pulled through the smaller channels 284 and 285. In one embodiment, the first end 302 and the second end 304 of the resilient member 300 have a donut shape with a pin in the center. In other embodiments, the first end 302 and second end 304 of the resilient member 300 can be clamped or bonded.

The resilient member 300 is elastic and provides resistance to the hinge members 260 and 261 during flexion. In one embodiment, urethane can be used; in other embodiments other materials may be used. The resilient member 300 stretches as the first hinge member 260 rotates in a direction $D_1$ and/or the second hinge member 261 rotates in a direction $D_2$. The resilient member 300 urges the first hinge member 260 to rotate in a direction $D_3$ and the second hinge member 261 to rotate in a direction $D_4$. Accordingly, when no external force is placed on the first and second hinge members 260 and 261, the pins 252 and 253 are drawn toward the first endpoints 224 and 225 of the slots 220 and 222. When an external force is applied to the first hinge member 260 causing rotation in the direction $D_1$, the resilient member 300 stretches elastically and rides along a curved edge 270 of the first hinge member 260. In the illustrated embodiment, the curved edge 270 has a radius $R_3$. In one embodiment, the curved edge 270 may not have a constant radius. Similarly, when an external force is applied to the second hinge member 261 causing rotation in the direction $D_2$, the resilient member 300 stretches elastically and rides along a curved edge 271 of the second hinge member 261. In the illustrated embodiment, the curved edge 271 has a radius $R_4$ that is greater than the radius $R_3$. In additional embodiments, the radius $R_3$ can be equal to or greater than the radius $R_4$.

The resilient member 300 and the radii of the hinge members 260 and 261 operate together to control the rotation of the hinge members 260 and 261. For example, when $R_3$ is less than $R_4$, the first hinge member 260 rotates in direction $D_1$ for an arc length before the second hinge member 261 rotates in direction $D_2$ for an arc length. This is because a greater external force must be applied to rotate a member with a greater radius in light of the counter force applied by the resilient member 300. Accordingly, in the illustrated embodiment, when an external force is applied to the hinge 310, the first hinge member 260 rotates first because its radius $R_3$ is less than the radius $R_4$ of the second hinge member 261. The second hinge member 261 will begin to rotate after the pin 252 of the first hinge member 260 has rotated through at least a portion of its range of motion. The rotation of one hinge member before the rotation of the other hinge member simulates the natural anatomical motion of the knee joint during extension and flexion. A better simulation of the natural motion of the knee joint reduces the movement of the knee brace down the leg of the user and the tendency of the knee brace to force the knee into unnatural positions.

Figure 3B:
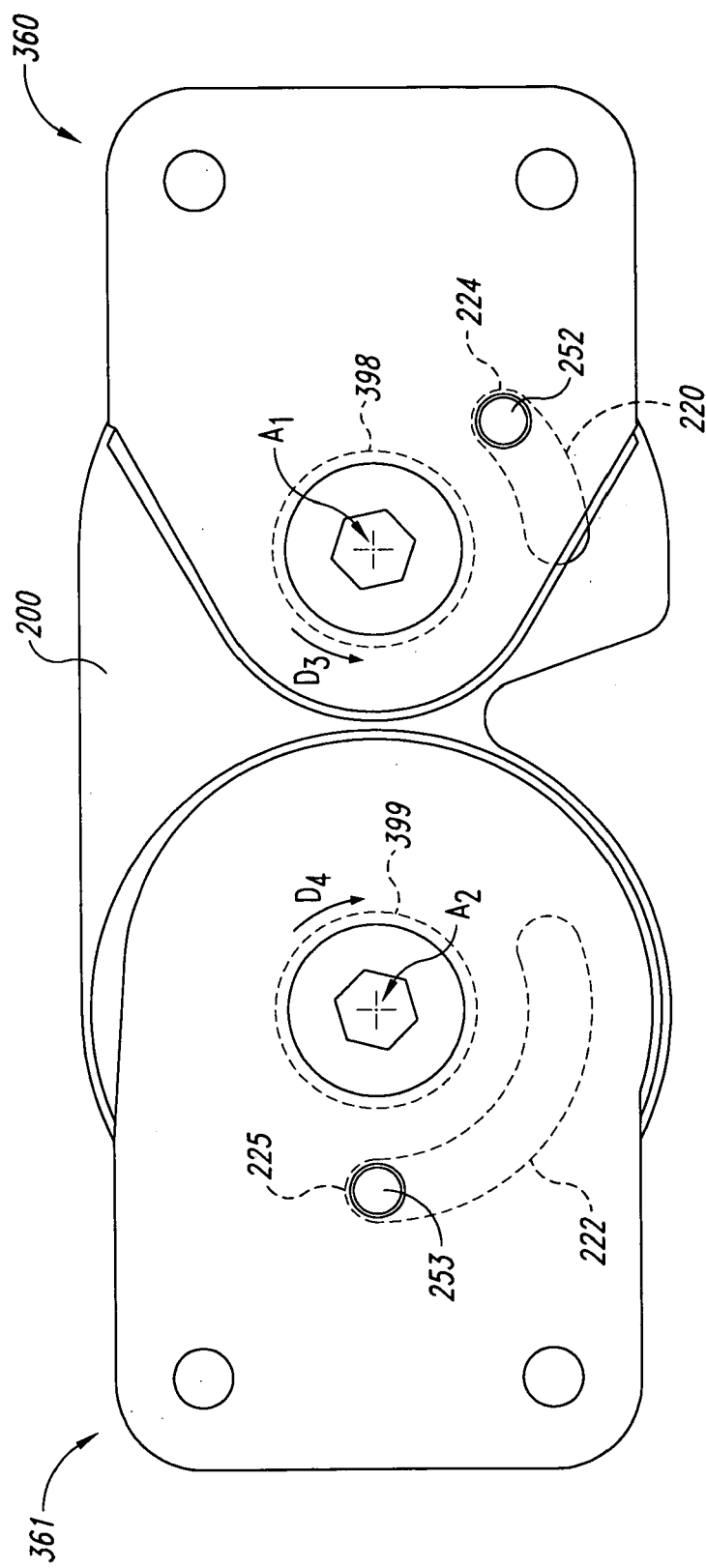
FIG. 3B is a top plan view of an assembly including a first torsion spring attached to a first hinge member and a second torsion spring attached to a second hinge member in accordance with another embodiment of the invention.

FIG. 3B is a top plan view of an assembly including a first torsion spring 398 attached to a first hinge member 360 and a second torsion spring 399 attached to a second hinge member 361 in accordance with another embodiment of the invention. Each torsion spring 398 and 399 is also attached to the back plate 200. The first torsion spring 398 urges the first hinge member 360 to rotate in the direction $D_3$ and the second torsion spring 399 urges the second hinge member to rotate in the direction $D_4$. Accordingly, when no external force is placed on the first and second hinge members 360 and 361, the pins 252 and 253 are drawn toward the first endpoints 224 and 225 of the slots 220 and 222. In one embodiment, the torsion springs can have different spring coefficients causing one hinge member to rotate before the other.

Figure 4:
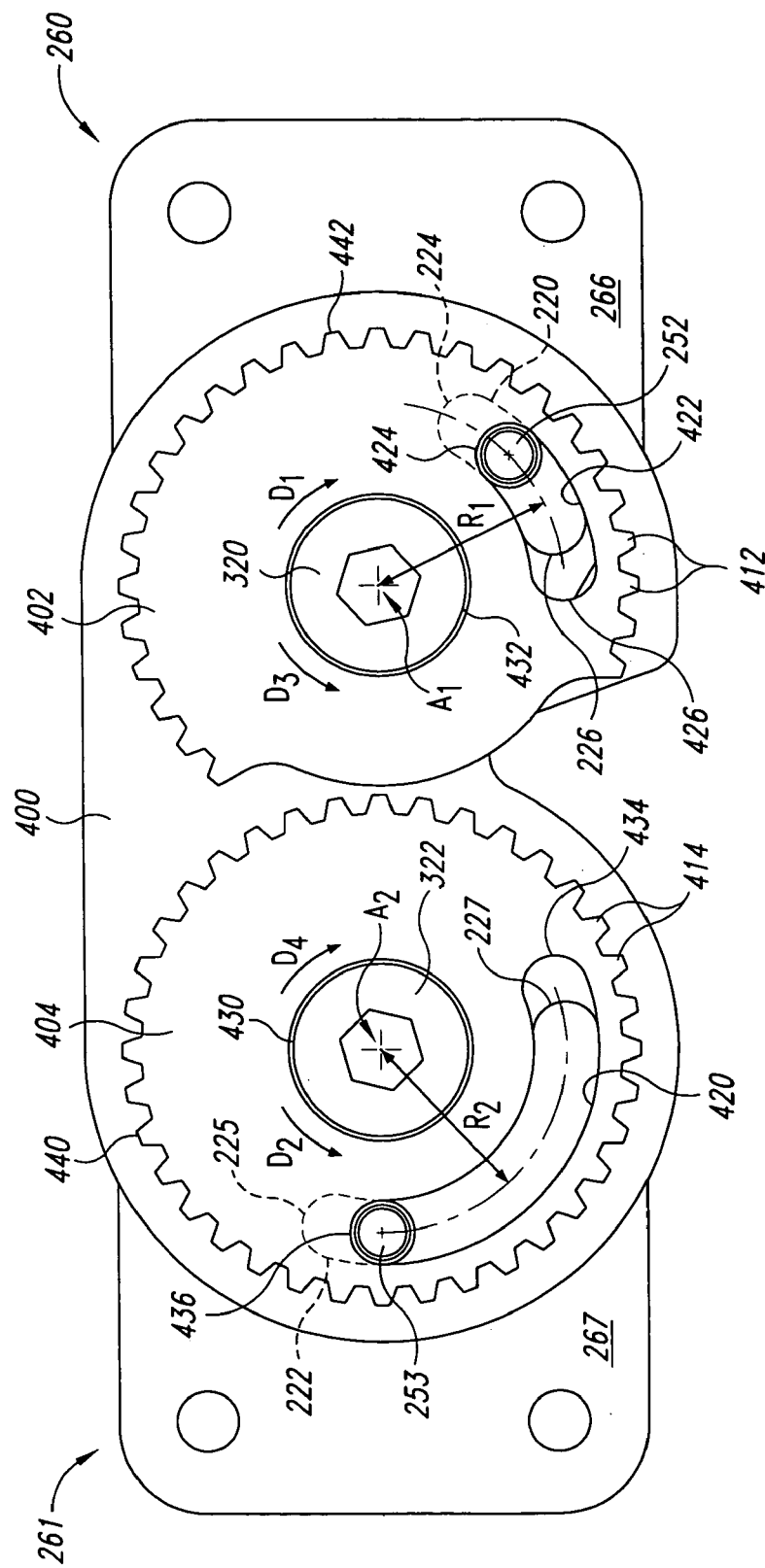
FIG. 4 is a top plan view of first and second adjustable range restrictors.
Figure 5B:
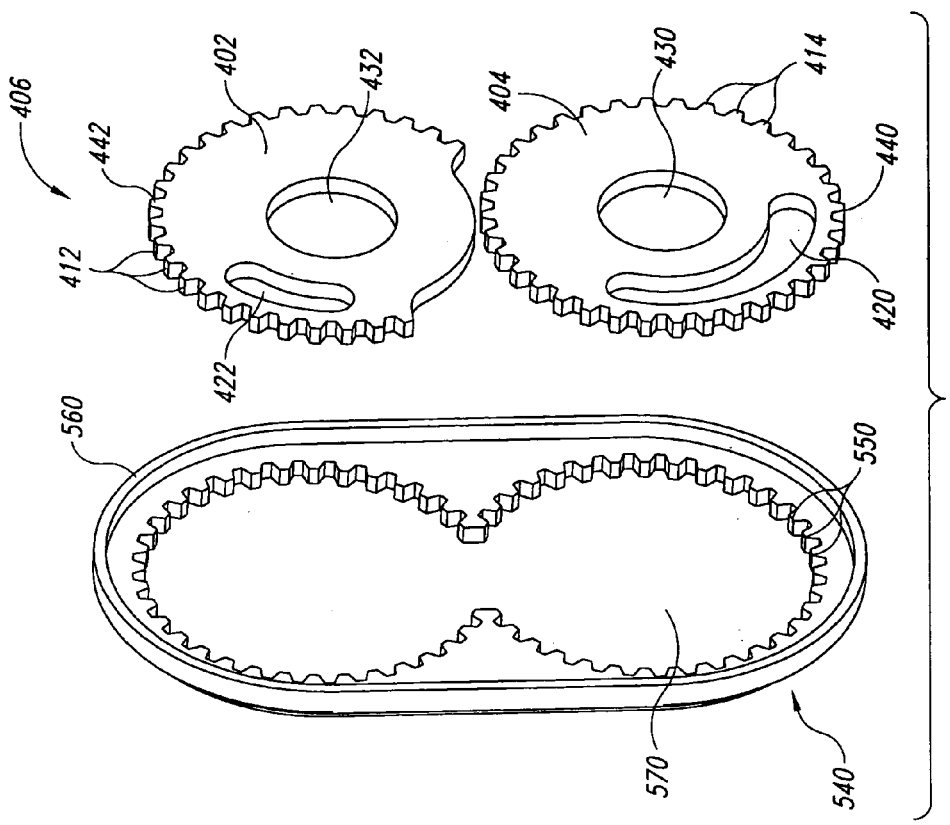
FIG. 5B is an isometric view of the adjustable range restrictor system of FIG. 5A with the first and second adjustable range restrictors removed from a cover plate.
Figure 5A:
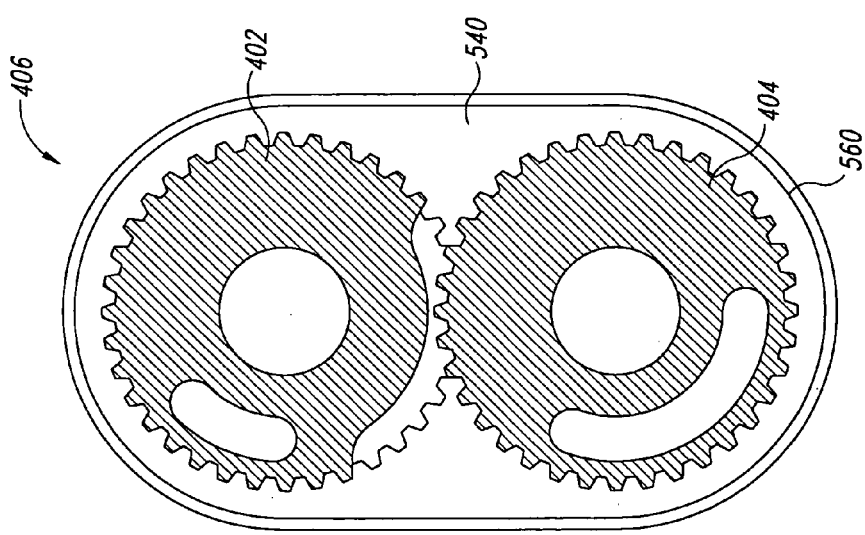
FIG. 5A is a top plan view of an adjustable range restrictor system in accordance with one embodiment of the invention.

FIG. 4 is a top plan view of the hinge 310 of FIG. 3A with first and second adjustable range restrictors 402 and 404. FIG. 5A is a top plan view of an adjustable range restrictor system 406 in accordance with one embodiment of the invention. FIG. 5B is an isometric view of the adjustable range restrictor system 406 of FIG. 5A with the first and second adjustable range restrictors 402 and 404 removed from a housing 540. As explained in more detail below, the adjustable range restrictor system 406 allows a user to adjust the pivoting range of the first hinge member 260 and/or the second hinge member 261.

Referring to the illustrated embodiment in FIG. 4, the fastener 320 is received in an aperture 432 of the first adjustable range restrictor 402 so that the first adjustable range restrictor 402 is positionable about the first axis of rotation $A_1$. The first adjustable range restrictor 402 has an annular slot 422 extending about the first axis of rotation $A_1$ with a centerline at the radius $R_1$. The slot 422 is positioned and sized to receive the pin 252 of the first hinge member 260. Accordingly, when the first hinge member 260 pivots, the pin 252 moves within the slot 422. Similarly, the fastener 322 is received in an aperture 430 of the second adjustable range restrictor 404 so that the second adjustable range restrictor 404 is positionable about the second axis of rotation $A_2$. The second adjustable range restrictor 404 has an annular slot 420 extending about the second axis of rotation $A_2$ with a centerline at the radius $R_2$. The slot 420 is positioned and sized to receive the pin 253 of the second hinge member 261. Accordingly, when the second hinge member 261 pivots, the pin 253 moves within the slot 420. In the illustrated embodiment, the length of the slot 420 is approximately equal to the length of the slot 222, and the length of the slot 422 is approximately equal to the length of the slot 220. In other embodiments, the slots 420 and 422 can have different lengths.

The first and second adjustable range restrictors 402 and 404 can be rotated so that their slots 422 and 420 limit the rotation of the first and second hinge members 260 and 261. For example, referring to the embodiment in FIG. 4, the first adjustable range restrictor 402 is positioned so that the slot 422 is offset from the slot 220 of the first hinge member 260. Consequently, a first endpoint 424 of the slot 422 and the second endpoint 226 of the slot 220 define stops for the pin 252 to limit the rotation of the first hinge member 260 about the first axis of rotation $A_1$. The first adjustable range restrictor 402 can be rotated further in the direction $D_1$ to further limit the rotation of the first hinge member 260. Conversely, the first adjustable range restrictor 402 can be rotated in the direction $D_3$ to increase the range of rotation. The second adjustable range restrictor 404 can similarly be positioned about the second axis of rotation $A_2$ so that the slot 420 is offset from the slot 222 to define stops for the pin 253 that limit the rotation of the second hinge member 261 about the second axis of rotation $A_2$.

The adjustable range restrictors 402 and 404 are held in place by the housing 540. Referring to FIGS. 5A and 5B, at least a portion of the outer edge 442 of the first adjustable range restrictor 402 has teeth 412, and the outer edge 440 of the second adjustable range restrictor 404 also has teeth 414. The housing 540 has a recess 570 with teeth 550 that engage the teeth 412 and 414 of the first and second adjustable range restrictors 402 and 404. When the housing 540 is attached to a front plate 400 (FIG. 4), the teeth 550 preclude the first and second adjustable range restrictors 402 and 404 from rotating about the first and second axes of rotation $A_1$ and $A_2$. The housing 540, for example, can have a lip 560 that snap-fits onto the front plate 400 to lock the first and second range restrictors 402 and 404 in the desired positions for limiting the range of motion. The first and second adjustable range restrictors 402 and 404 are rotatably adjusted by removing the housing 540, rotating the first and second adjustable range restrictors 402 and 404, and replacing the housing 540. The configuration of the teeth 412, 414 and 550 in the illustrated embodiment permits the first and second adjustable range restrictors 402 and 404 to be adjusted in 10-degree increments. In additional embodiments, the teeth 412, 414 and 550 can be sized and spaced differently.

One advantage of the embodiment of the range restrictor system 406 shown in FIGS. 4–5B is the ease with which a user can adjust the pivoting range of the first and second hinge members 260 and 261. It will be appreciated that the range restrictor system 406 can have other configurations. For example, in additional embodiments, other types of devices can be used to restrict the first and second adjustable range restrictors 402 and 404 from rotating about the first and second axes of rotation $A_1$ and $A_2$. In one such embodiment, the front plate 400 could have a projection with teeth that engage the teeth of one or both of the adjustable range restrictors 402 and 404, thus eliminating the need for the housing 540. In the illustrated embodiment, the front plate 400 is similar to the back plate 200, but is positioned on the other side of the hinge members 260 and 261. In still other embodiments, the front plate 400 can have a different configuration, or the hinge may not have the front plate 400. In further embodiments, the first and second adjustable range restrictors 402 and 404 can be placed proximate to the first and second hinge members 260 and 261, or the adjustable range restrictor system 406 can be placed adjacent to the back surface of the back plate 200. In additional embodiments, the hinge may not have the adjustable range restrictor system 406.

Figure 6:
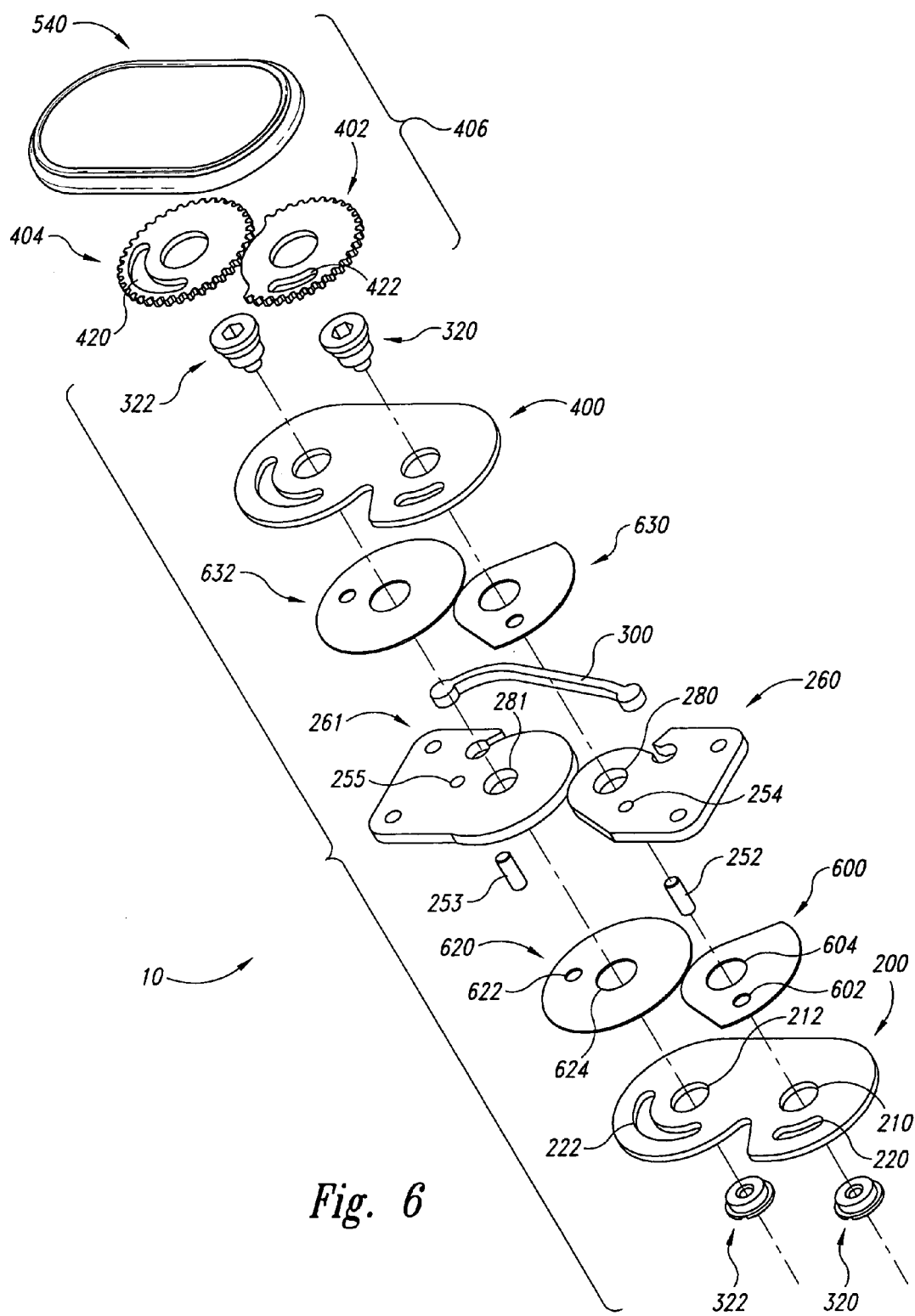
FIG. 6 is an isometric exploded view of a hinge and range restrictor in accordance with an embodiment of the invention.

FIG. 6 is an exploded view of the hinge 10 of FIG. 1. In the illustrated embodiment, the first and second hinge members. 260 and 261 are held between the back plate 200 and the front plate 400 by the fasteners 320 and 322. The hinge 10 can have spacers 600, 620, 630 and 632 to assist the first and second hinge members 260 and 261 to rotate more easily between the plates 400 and 200. The spacers 600 and 630 have an aperture 604 through which the fastener 320 is placed, and an aperture 602 through which the first pin 252 is placed. Similarly, the spacers 620 and 632 have an aperture 624 through which the fastener 322 is placed, and an aperture 622 through which the second pin 253 is placed. In additional embodiments, the spacers 600, 620, 630 and 632 can have different configurations, or the hinge 10 may not have one or more of the spacers 600, 620, 630 and 632. The range restrictor system 406 attaches to the front plate 400 as explained above.

FIG. 6 also illustrates the compactness of the hinge 10 and the range restrictor system 406. The hinge 10 and the range restrictor system 406 together can have a thickness of between 0.125 inch and 1 inch. In one embodiment, the hinge 10 and the range restrictor system 406 together have a thickness of approximately 0.31 inch. The compact size of the hinge 10 and the range restrictor system 406 makes it easier to wear clothes over the knee brace and reduces the risk of the hinge interfering with the other knee joint during activities.

Figure 7A:
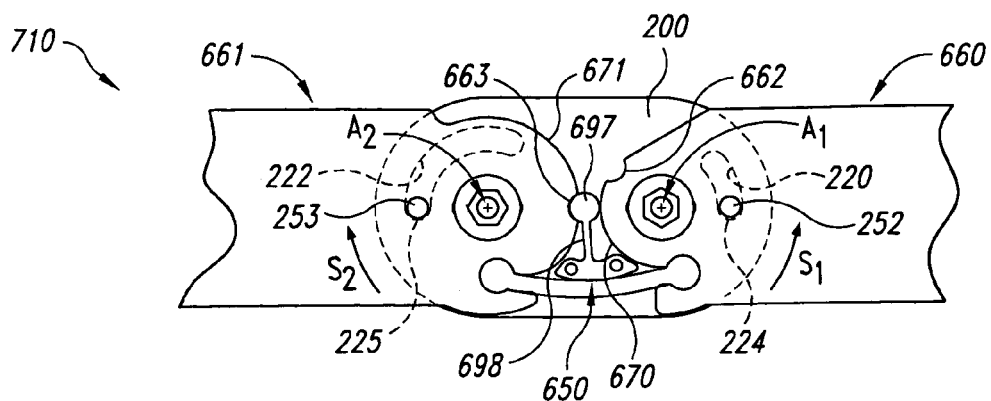
FIGS. 7A–7C are top plan views illustrating a hinge with a rocker in accordance with another embodiment of the invention.
Figure 7B:
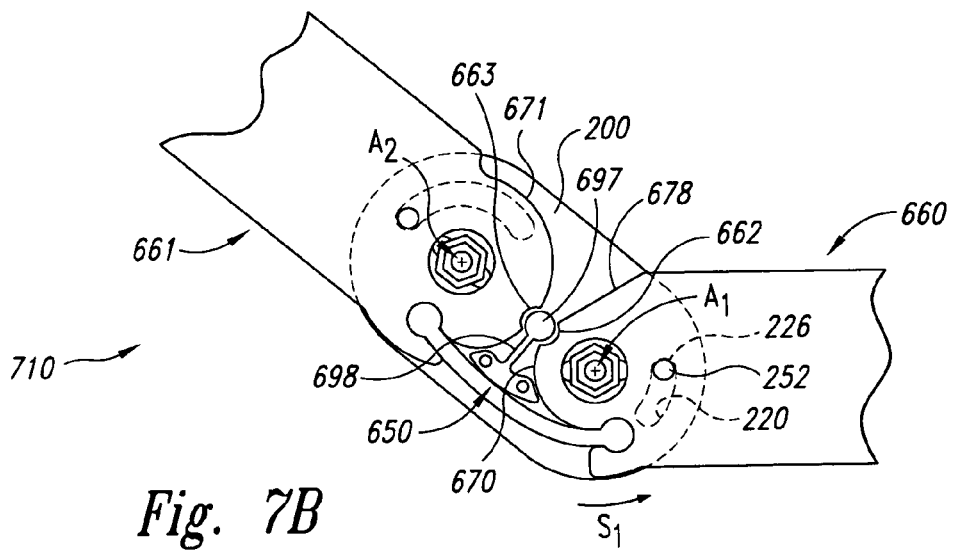
Figure 7C:
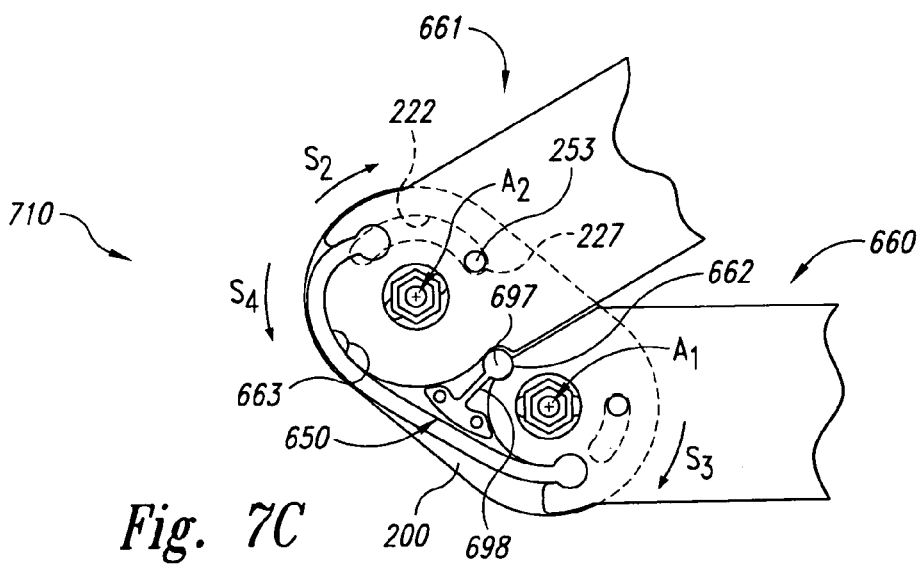

FIGS. 7A–7C are top plan views illustrating a hinge 710 in accordance with another embodiment of the invention. The hinge 710 is similar to the hinge 10 described above, and like reference numbers refer to like components in FIGS. 1–7C. In the illustrated embodiment, the hinge 710 includes a first hinge member 660 with a first recess 662 and a second hinge member 661 with a second recess 663. The first and second hinge members 660 and 661 are pivotally coupled to the back plate 200. Referring to FIG. 7A, the pin 252 of the first hinge member 660 is positioned at the first endpoint 224 of the slot 220 in the back plate 200, and the pin 253 of the second hinge member 661 is positioned at the first endpoint 225 of the slot 222 in the back plate 200. The hinge 710 also includes a rocker 650 attached to the back plate 200. The rocker 650 has a flexible arm 698 and a head 697 positioned between the first hinge member 660 and the second hinge member 661.

When the hinge 710 is in the full-extension position shown in FIG. 7A, the head 697 is proximate to a curved edge 670 of the first hinge member 660 and at least partially within the second recess 663 of the second hinge member 661. Because the head 697 of the rocker 650 is at least partially within the second recess 663 of the second hinge member 661, the second hinge member 661 is effectively jammed and restricted from movement. Accordingly, a force applied to either hinge member 660 or 661 will cause the first hinge member 660 to pivot in a direction $S_1$ about the first axis of rotation $A_1$.

Referring to FIG. 7B, the first hinge member 660 has pivoted about the first axis of rotation $A_1$ to a position where the pin 252 is at the second endpoint 226 of the slot 220 in the back plate 200. The first hinge member 660 accordingly cannot pivot further about the first axis of rotation $A_1$ in the direction $S_1$. In this position, the head 697 of the rocker 650 is received at least partially within the first recess 662 of the first hinge member 660, releasing the bending force on the arm 698. In this position the head 697 is free to move between the two recesses 662 and 663. As the second hinge member 261 begins to rotate about the second axis of rotation $A_2$, the cam shape of the surface 671 forces the head 697 of the rocker 650 into the first recess 662 of the first hinge member 660, effectively jamming and precluding rotation of the first hinge member 660 about the first axis of rotation $A_1$.

Referring to FIG. 7C, the second hinge member 661 has pivoted about the second axis of rotation $A_2$ to a position where the pin 253 is at the second endpoint 227 of the slot 222 in the back plate 200. The second hinge member 661 accordingly cannot pivot further about the second axis of rotation $A_2$ in the direction $S_2$. Throughout the rotation of the second hinge member 661 from the position in FIG. 7B to the position in FIG. 7C, the head 697 of the rocker 650 remains in the first recess 662 of the first hinge member 660 precluding the first hinge member 660 from pivoting about the first axis of rotation $A_1$. Because the head 697 of the rocker 650 is at least partially within the first recess 662 of the first hinge member 660, the first hinge member 660 requires a greater force to rotate in a direction $S_3$ than the force required for the second hinge member 661 to rotate in a direction $S_4$. Accordingly, the rocker 650 encourages the second hinge member 661 to pivot in the direction $S_4$ about the second axis of rotation $A_2$ before the first hinge member 660 pivots in the direction $S_3$ about the first axis of rotation $A_1$. In additional embodiments, the hinge 710 can have a rocker with a different configuration, or the hinge may not have a rocker. Furthermore, FIGS. 7A–7C illustrate the full range of extension (FIGS. 7A–B) and flexion (FIGS. 7B–C) of the illustrated embodiment. Other embodiments can also have this range of extension and flexion without the rocker 650 or other components.

Figure 8:
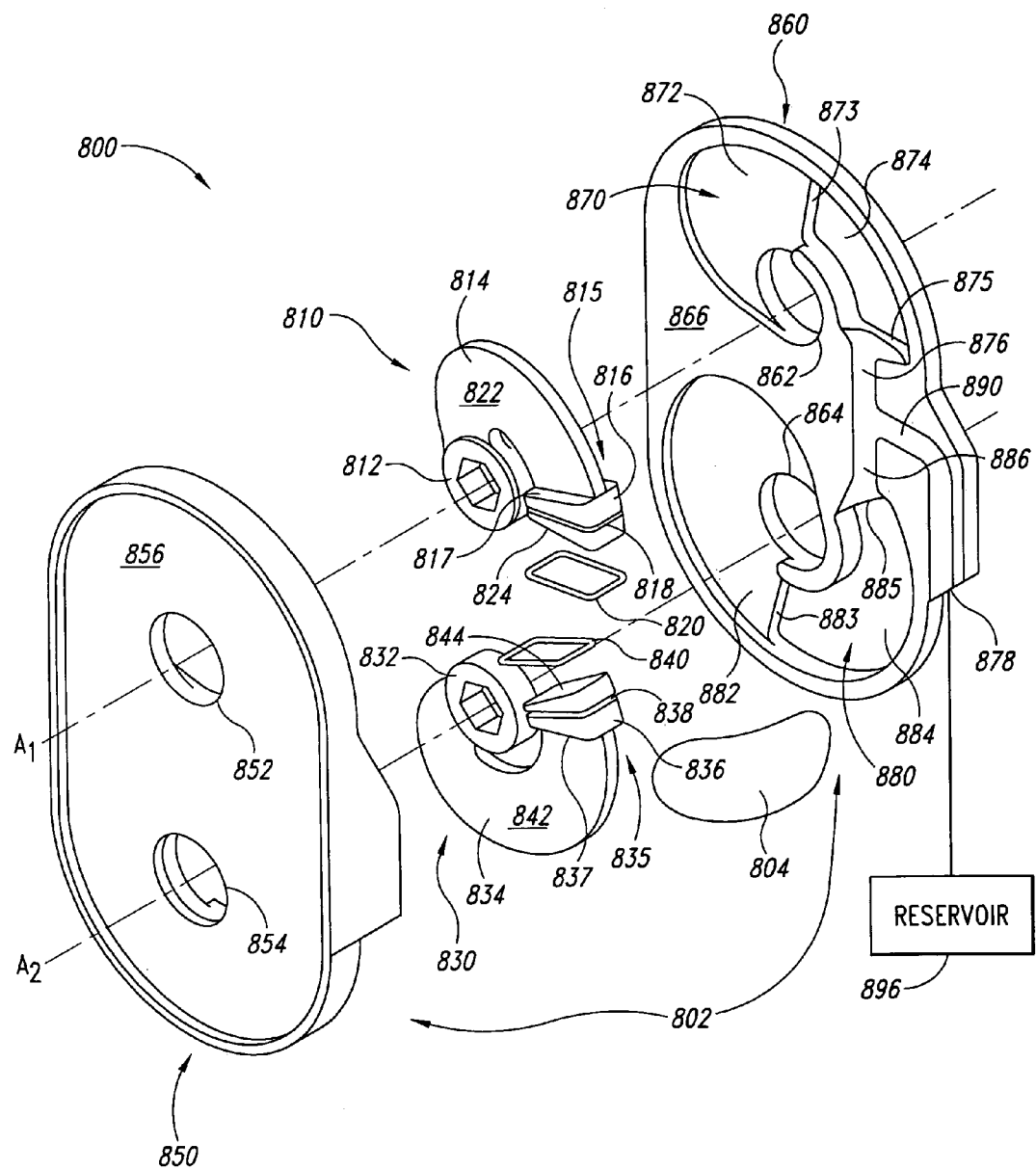
FIG. 8 is an isometric exploded view of a power pack in accordance with one embodiment of the invention.

FIG. 8 is an isometric exploded view of a power pack 800 in accordance with one embodiment of the invention that can be used with embodiments of the hinges 10 and 710 described above, and also with other types of single axis or bicentric hinges. In the illustrated embodiment, the power pack 800 includes a first piston 810, a second piston 830, and a housing 802 having a front portion 850 and a rear portion 860. The first piston 810 in the embodiment shown in FIG. 8 is a rotary piston that is received within an upper cavity 870 in a front side 866 of the rear portion 860 of the housing 802, and a similar cavity (not shown) in the backside (not shown) of the front portion 850 of the housing 802. Similarly, the second piston 830 in the embodiment shown in FIG. 8 is a rotary piston that is received within a lower cavity 880 in the front side 866 of the rear portion 860 of the housing 802 and a similar cavity (not shown) in the backside (not shown) of the front portion 850 of the housing 802. In other embodiments, the pistons can be linear pistons, and a portion of the pistons can extend outside the housing 802.

The first piston 810 of the illustrated embodiment includes a hub 812, an arm 814 attached to the hub 812, and a head 816 attached to a distal portion 815 of the arm 814. A portion of the hub 812 projects beyond a back surface (not shown) of the arm 814 and is received within an aperture 862 in the rear portion 860 of the housing 802. Another portion of the hub 812 projects beyond a front surface 822 of the arm 814 and is received within an aperture 852 in the front portion 850 of the housing 802. The apertures 852 and 862 and the hub 812 are aligned with the first axis of rotation $A_1$ about which the first piston 810 rotates. The arm 814 of the first piston 810 is received within a channel 872 in the upper cavity 870 of the housing 802. The channel 872 is sized and configured to permit the arm 814 to pivot about the first axis of rotation $A_1$. The head 816 of the piston 810 is received within an annular chamber 874 in the upper cavity 870 of the housing 802 in this embodiment. The annular chamber 874 is sized and configured to permit the head 816 to pivot about the first axis of rotation $A_1$. As the first piston 810 rotates about the first axis of rotation $A_1$, the head 816 moves through the annular chamber 874 from a position in which a surface 817 on the head 816 contacts a first wall 873 in the chamber 874 to a position in which a top surface 824 on the head 816 contacts a second wall 875 in the chamber 874. Thus, the first wall 873 and the second wall 875 of the chamber 874 define the stops for the first piston 810.

The second piston 830 of the illustrated embodiment includes a hub 832, an arm 834 attached to the hub 832, and a head 836 attached to a distal portion 835 of the arm 834. A portion of the hub 832 projects beyond a back surface (not shown) of the arm 834 and is received within an aperture 864 in the rear portion 860 of the housing 802. Another portion of the hub 832 projects beyond a front surface 842 of the arm 834 and is received within an aperture 854 in the front portion 850 of the housing 802. The apertures 854 and 864 and the hub 832 are aligned with the second axis of rotation $A_2$ about which the second piston 830 rotates. The arm 834 of the second piston 830 is received within a channel 882 in the lower cavity 880 of the housing 802. The channel 882 is sized and configured to permit the arm 834 to pivot about the second axis of rotation $A_2$. The head 836 of the second piston 830 is received within an annular chamber 884 in the lower cavity 880 of the housing 802 in this embodiment. The annular chamber 884 is sized and configured to permit the head 836 to pivot about the second axis of rotation $A_2$. As the second piston 830 rotates about the second axis of rotation $A_2$, the head 836 moves through the annular chamber 884 from a position in which a surface 837 on the head 836 contacts a first wall 883 in the chamber 884 to a position in which a top surface 844 on the head 836 contacts a second wall 885 in the chamber 884. Thus, the first wall 883 and the second wall 885 of the chamber 884 define the stops for the second piston 830.

In the illustrated embodiment, the first and second pistons 810 and 830 are the same size and shape. In additional embodiments, the pistons 810 and 830 can be shaped or configured differently. For example, one piston can have an annular arm with a greater radius than the arm of the other piston, or one piston can have a head with a different size or shape than the head of the other piston. In still other embodiments, the power pack can have only one piston. In the illustrated embodiment, the annular chamber 884 in the upper cavity 870 has a longer arc length than the annular chamber 874 in the lower cavity 880, and the upper annular channel 882 is bigger than the lower annular channel 872. These differences in size allow the second piston 830 to pivot further about the second axis of rotation $A_2$ than the first piston can pivot about the first axis of rotation $A_1$. In additional embodiments, the range of pivot and the size of the channels and chambers can be the same. Or alternatively, the first piston 810 can have a greater range of pivot than the second piston 830. In additional embodiments, the housing may not have a channel, or the channel and chamber can be shaped or configured differently. For example, the chamber can be linear rather than annular.

The annular chamber 874 of the upper cavity 870 is configured to receive and hold a fluid (not shown). In one embodiment, the fluid is a mineral oil; in other embodiments, water or hydraulic fluids can be used. The fluid is displaced from the chamber 874 into an upper fluid passageway 876 as the head 816 moves through the annular chamber 874 when the first piston 810 rotates about the first axis of rotation $A_1$. The fluid flows from the upper fluid passageway 876 through a side fluid passageway 890 to an outlet 878 that is coupled to a reservoir 896. Similarly, the annular chamber 884 of the lower cavity 880 is configured to receive and hold the fluid. In the illustrated embodiment, the annular chamber 884 includes a rolling bladder 804. In other embodiments, both annular chambers can include a sleeve or a bladder, or the chambers may not include either. In the illustrated embodiment, the fluid is displaced from the chamber 884 into a lower fluid passageway 886 as the head 836 moves through the annular chamber 884 when the second piston rotates 830 about the second axis of rotation $A_2$. The fluid flows from the lower fluid passageway 886 through the side fluid passageway 890 to the outlet 878. In additional embodiments, the upper fluid passageway 876 and the lower fluid passageway 886 can remain separate, and each passageway 876 and 886 can have a separate outlet and reservoir.

In the illustrated embodiment, the heads 816 and 836 of the first and second pistons 810 and 830 have rectangular cross-sectional shapes to provide more surface area in the small space within the housing 802. Furthermore, in the illustrated embodiment, the heads 816 and 836 have grooves 818 and 838 to receive seals 820 and 840. The seals 820 and 840 prevent fluid from leaking into the channels 872 and 884. In additional embodiment, the heads 816 and 836 can have different cross-sectional shapes such as a circular shape. In other embodiments, the heads 816 and 836 may not have seals or may have different seals.

Figure 9:
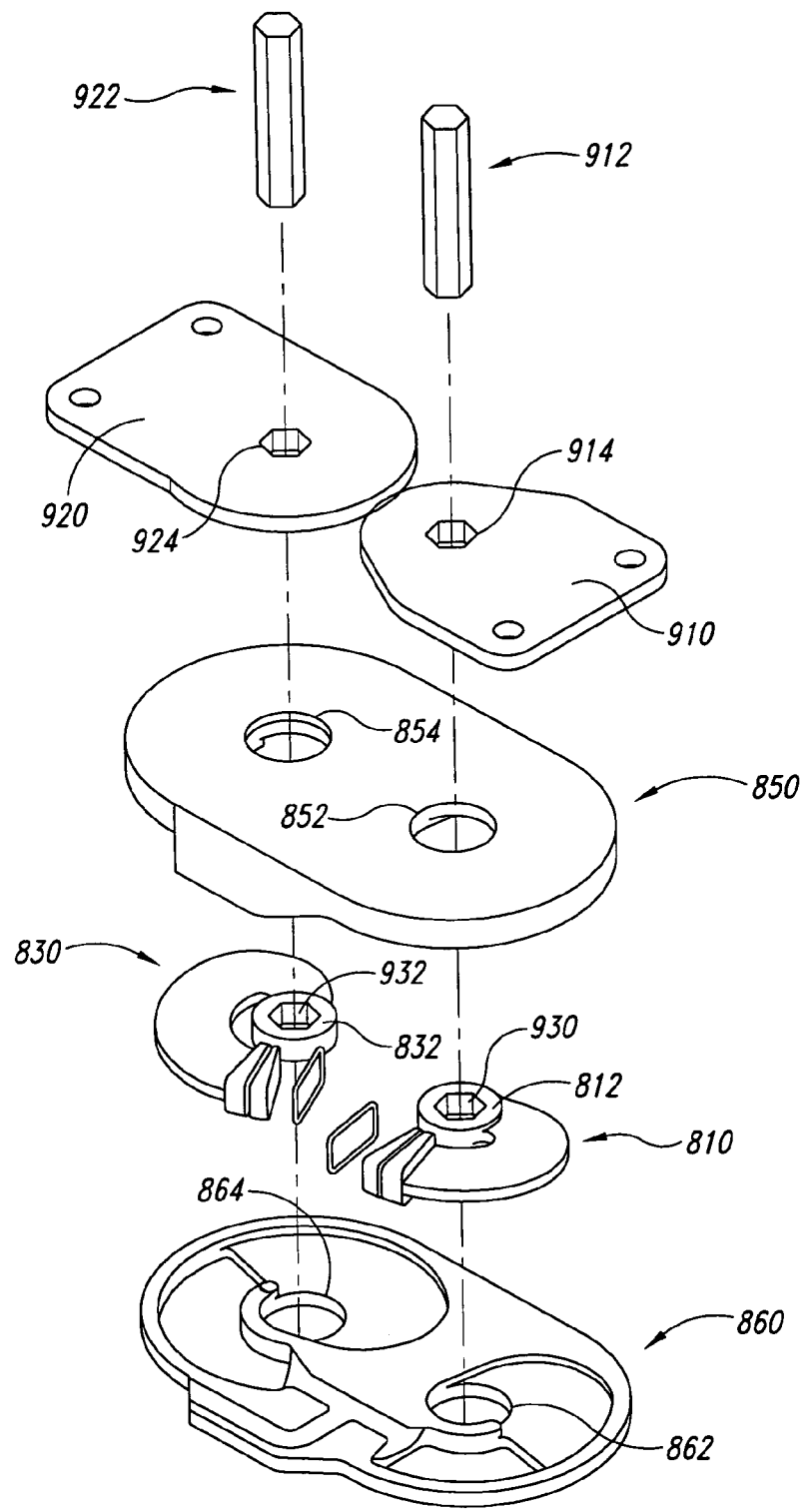
FIG. 9 is an isometric exploded view of a hinge having a power pack, a first hinge member, and a second hinge member in accordance with one embodiment of the invention.

FIG. 9 is an isometric exploded view of the connection between the power pack 800, a first hinge member 910, and a second hinge member 920 in accordance with one embodiment of the invention. The first hinge member 910 and the second hinge member 920 can be used in the hinges 10 and 710 described above, or they can be used in different bicentric hinges (including geared or non-geared hinges). In the illustrated embodiment, a first rod 912 couples the first hinge member 910 to the hub 812 of the first piston 810. The first rod 912 is received within an aperture 914 in the first hinge member 910 and an aperture 930 in the hub 812 of the first piston 810. Similarly, a second rod 922 couples the second hinge member 920 to the hub 832 of the second piston 830. The second rod 922 is received within an aperture 924 in the second hinge member 920 and an aperture 932 in the hub 832 of the second piston 830. In the illustrated embodiment, the rods 912 and 922 and the apertures 914, 924, 930 and 932 are hexagonal so that the rods 912 and 922 translate rotation of the hinge members 910 and 920 to the pistons 810 and 830. In other embodiments, the pistons 810 and 830 can be coupled to the hinge members 910 and 920 by other methods. For example, the pistons, rods, and hinge member can be rotatably coupled with a keyway-spline connection.

Figure 10A:
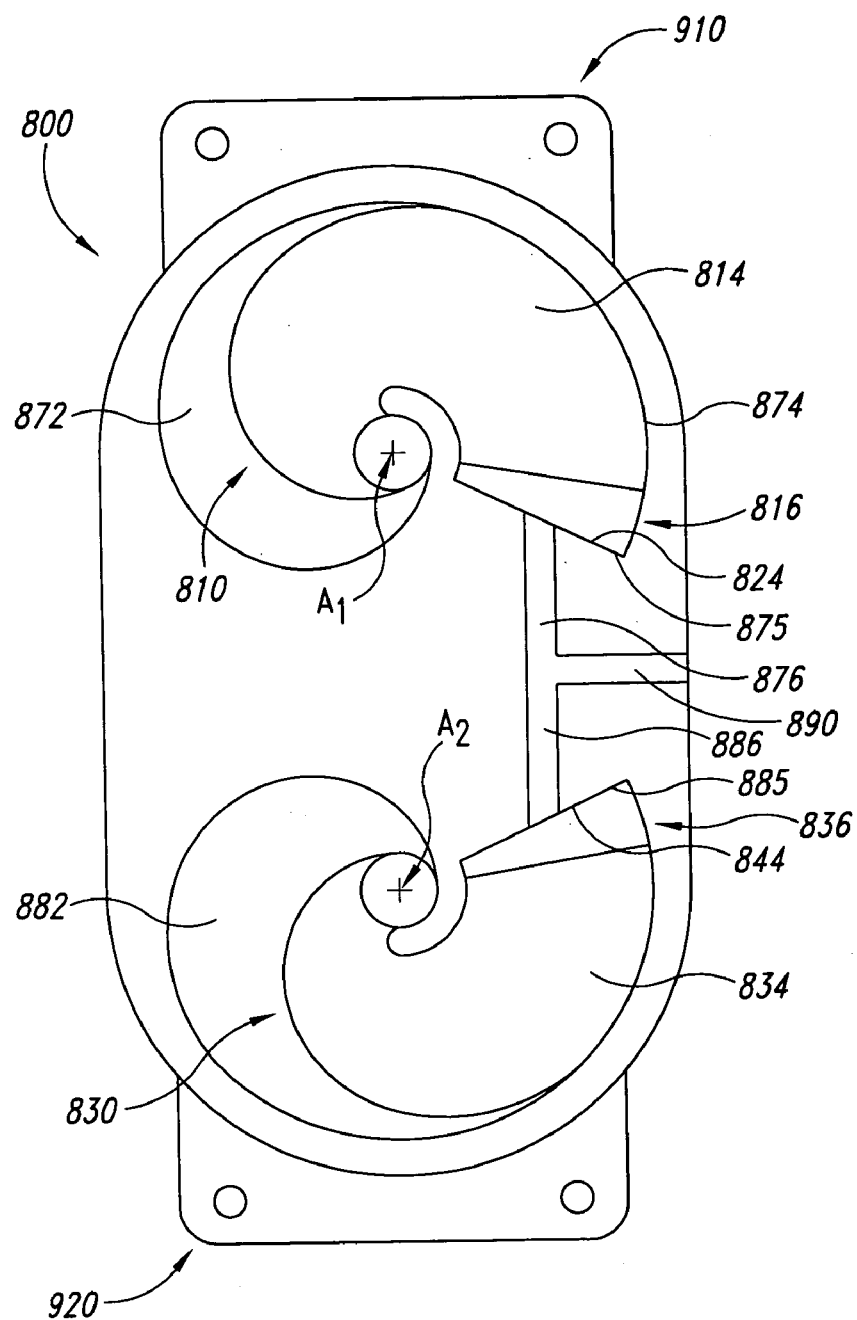
FIGS. 10A–10C are top plan views of a power pack attached to a first hinge member and a second hinge member in accordance with another embodiment of the invention.
Figure 10B:
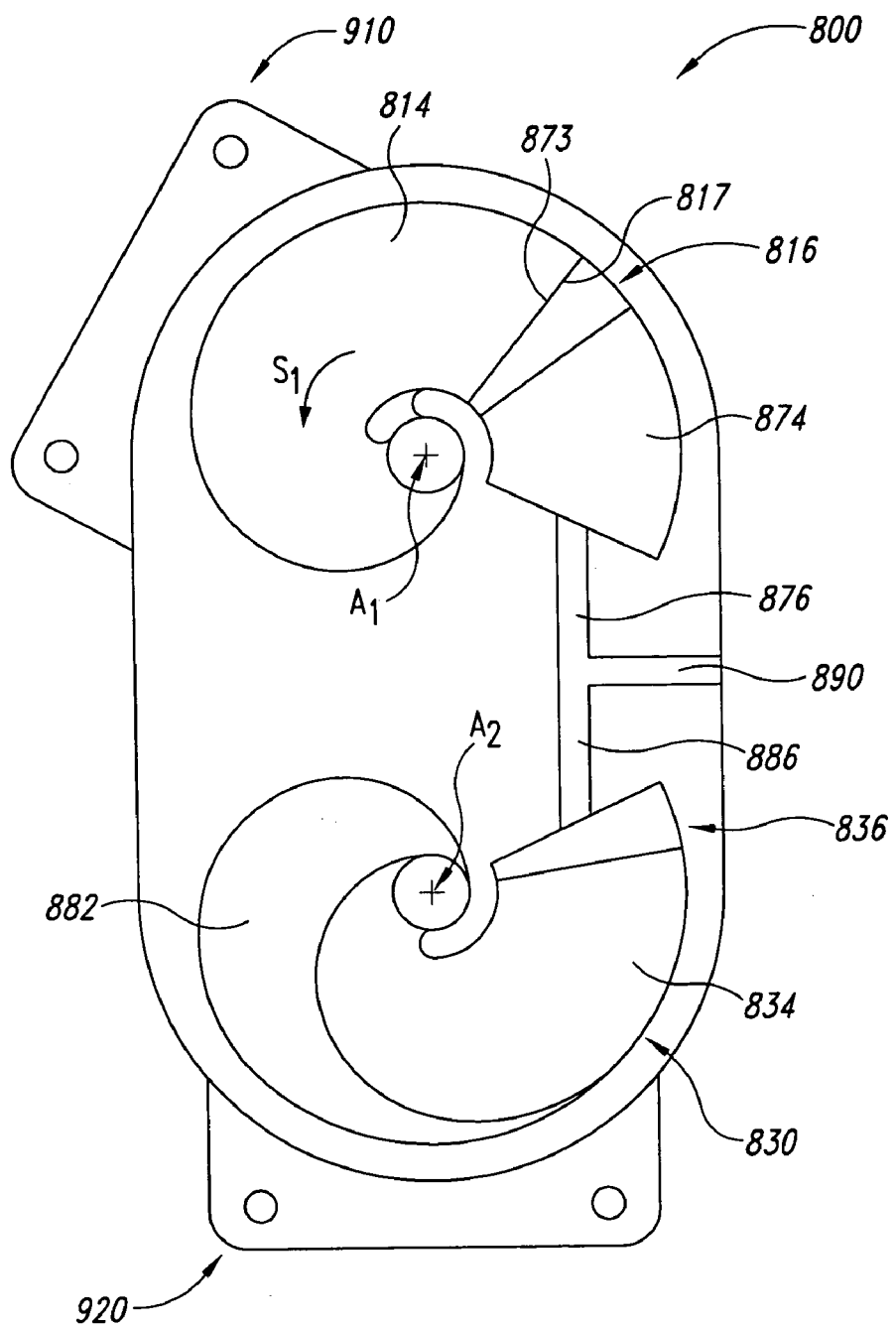
Figure 10C:
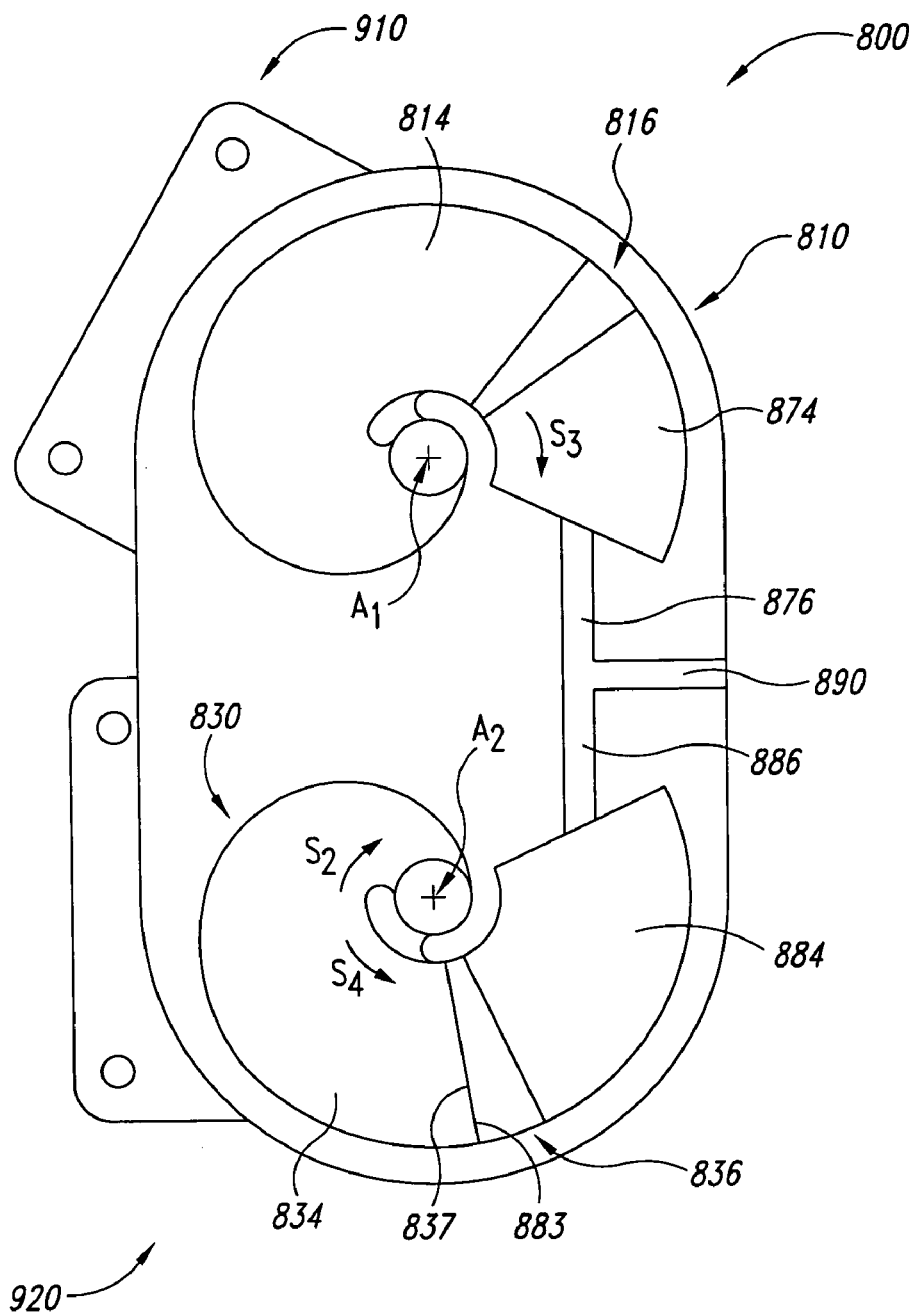

FIGS. 10A–10C are top plan views of the power pack 800 attached to the first hinge member 910 and the second hinge member 920. FIG. 10A illustrates the power pack 800 when the first and second hinge members 910 and 920 are in the full-extension position (i.e., corresponding to full leg extension). The first piston 810 is accordingly positioned so that the top surface 824 of the head 816 contacts the second wall 875 of the chamber 874. The second piston 830 is similarly positioned so that the top surface 844 of the head 836 contacts the second wall 885 of the chamber 884. As a result, the fluid is displaced from the chambers 874 and 884 when the hinge members 910 and 920 are in the full-extension position.

FIG. 10B illustrates the power pack 800 when the first and second hinge members 910 and 920 are in an intermediate position between full-extension and full-flexion. The rotation of the first hinge member 910 in the direction $S_1$ about the first axis of rotation $A_1$ moves the first piston 810 from the position illustrated in FIG. 10A to the position illustrated in FIG. 10B. As the first piston 810 rotates, the head 816 moves through the annular chamber 874 drawing the fluid into the chamber 874 from the upper fluid passageway 876. The first piston 810 continues to rotate until the surface 817 of the head 816 contacts the first wall 873 of the chamber 874. The first wall 873 of the chamber 874 precludes further rotation of the first piston 810, and consequently the first hinge member 910, about the first axis of rotation $A_1$ in the direction $S_1$.

FIG. 10C illustrates the power pack 800 when the first and second hinges 910 and 920 are in the full-flexion position. The rotation of the second hinge member 920 in the direction $S_2$ about the second axis of rotation $A_2$ moves the second piston 830 from the position illustrated in FIG. 10B to the position illustrated in FIG. 10C. As the second piston 830 rotates, the head 836 moves through the annular chamber 884 drawing the fluid into the chamber 884 from the lower fluid passageway 886. In other embodiments, the second piston 830 can rotate before the first piston 810 rotates. Referring to FIG. 10C, the second piston 830 is illustrated in a position with the surface 837 of the head 836 contacting the first wall 883 in the lower annular chamber 884. The first wall 883 of the chamber 884 precludes further rotation of the second piston 830, and consequently the second hinge member 920, about the second axis of rotation $A_2$ in the direction $S_2$. From the position illustrated in FIG. 10C the first piston 810 can displace the fluid from the chamber 874 by rotating about the first axis of rotation $A_1$ in the direction $S_3$ to the position illustrated in FIG. 10A. Similarly, the second piston 830 and the second hinge member 920 can displace the fluid from the chamber 884 by rotating about the second axis of rotation $A_2$ in the direction $S_4$ to the position illustrated in FIG. 10A.

Figure 11:
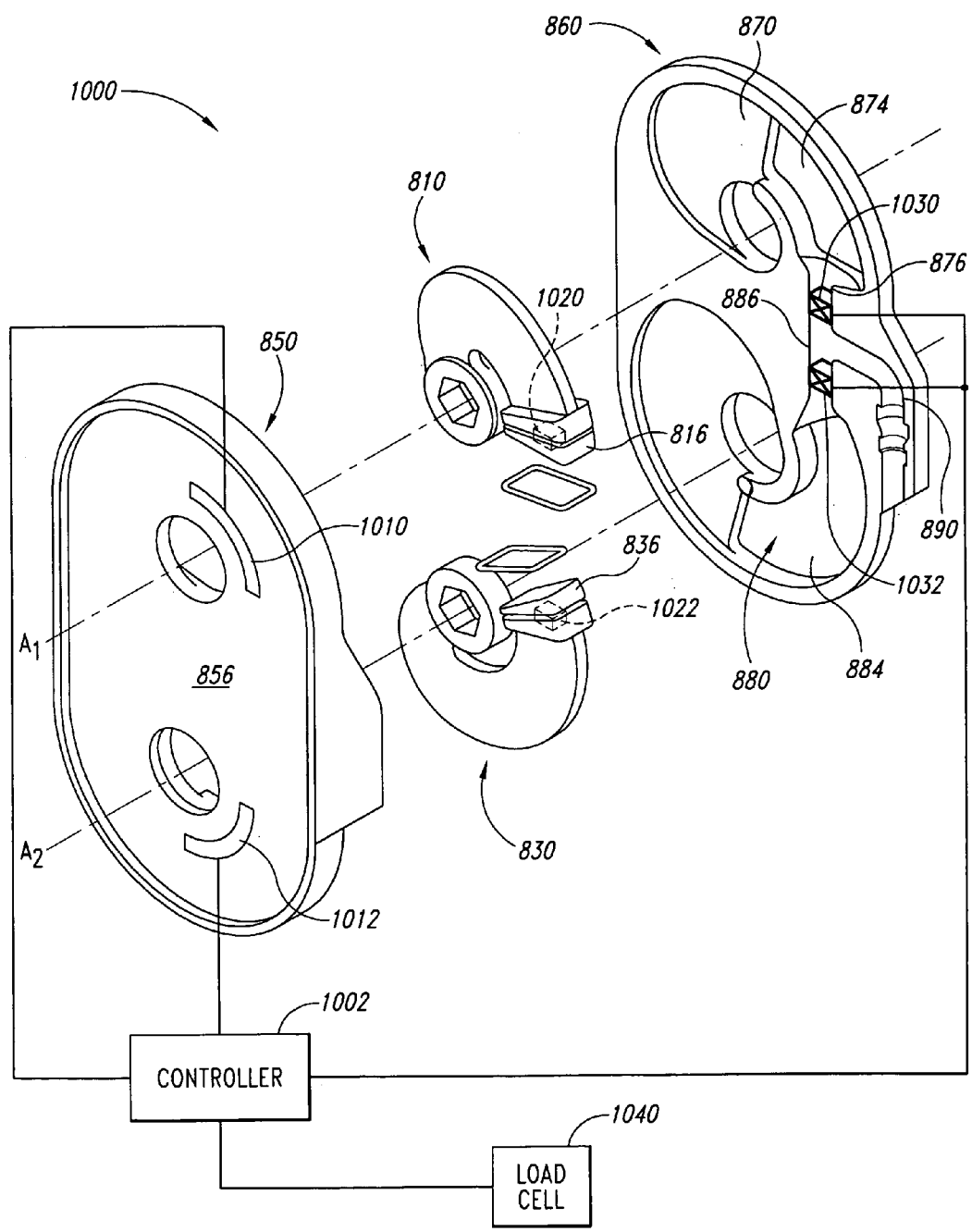
FIG. 11 is an isometric exploded view of a power pack having valves to control the fluid flow in accordance with another embodiment of the invention.

FIG. 11 is an isometric exploded view of a power pack 1000 having valves 1030 and 1032 to control the fluid flow in accordance with another embodiment of the invention. The power pack 1000 is similar to the power pack 800 described above, and like reference numbers refer to like components in FIGS. 8–11. The power pack 1000 of the illustrated embodiment has a first valve 1030 in the upper fluid passageway 876 and a second valve 1032 in the lower fluid passageway 886. The valves 1030 and 1032 control the fluid flow through the respective fluid passageways 876 and 886. When the upper valve 876 is partially closed, the fluid flow through the upper fluid passageway 876 is restricted, and consequently, the head 816 of the first piston 810 moves at a reduced speed within the chamber 874. When the upper valve 876 is closed, no fluid can flow through the upper fluid passageway 876, and consequently, the head 816 of the first piston 810 cannot move within the chamber 874.

Accordingly, the valves 1030 and 1032 can control the ability of the pistons 810 and 830, and therefore the hinge members 910 and 920 (FIG. 9), to rotate about the first and second axes of rotation $A_1$ and $A_2$. Furthermore, the valves 1030 and 1032 can control the speed at which the hinge members 910 and 920 rotate. In one embodiment, the valves 1030 and 1032 can be piezoelectric valves. In another embodiment, the power pack 1000 can have other valves or only one valve.

In the illustrated embodiment, the valves 1030 and 1032 are controlled by a controller 1002. The controller 1002 can be a programmable chip with memory that is mounted on or in the housing 802. The controller 1002 can be programmed using a separate hand-set with an infrared link or a hard-wired link.

The controller 1002 can communicate with the valves 1030 and 1032 through a wired, wireless, or infrared connection. Thus, as explained below, the controller 1002 can control the rotation of the first and second hinge members 910 and 920 by restricting or stopping the flow of fluid through the valves 1030 and 1032.

In the illustrated embodiment, the power pack 1000 contains a system to automatically adjust the valves 1030 and 1032 to a particular setting corresponding to the position of the heads 816 and 836 in the chambers 874 and 834. The system includes a first magnet 1020 disposed in the head 816 of the first piston 810 and a second magnet 1022 disposed in the head 836 of the second piston 830. The front portion 850 of the housing 802 contains magnetic strips 1010 and 1012 positioned adjacent to the chambers 874 and 884. The magnetic strips 1010 and 1012 sense the location of the magnets 1020 and 1022, and consequently the position of the heads 816 and 836. The magnetic strips 1010 and 1012 can communicate with the controller 1002 through a wired, wireless, or infrared connection. Accordingly, the valves 1030 and 1032 can be adjusted to a particular setting corresponding to the position of the heads 816 and 836. In other embodiments, other position sensing devices can be used.

The ability to adjust the valves 1030 and 1032 depending on the location of the heads 816 and 836 allows the power pack 1000 to slow the pistons 810 and 830 and the first and second hinge members 910 and 920 before they reach the range of motion stops. For example, if a user is participating in a vigorous activity such as skiing, the power pack 1000 can slow the rotation of the hinge members 910 and 920, and accordingly the movement of the knee joint, before the hinge members 910 and 920 reach the range of motion stops. In other embodiments, the power pack 1000 can slow the rotation of the hinge members 910 and 920 when a user begins rotating the hinge members 910 and 920 at a speed that could result in a knee injury. Braking or slowing the hinge members 910 and 920 before the rotation stops can reduce the high loads in the knee joint and the knee brace caused by abrupt stops. Moreover, braking can reduce the risk of hyperextension in the knee joint. Furthermore, the ability to adjust the valves 1030 and 1032 based on a corresponding position of the heads 816 and 836 also allows a user to have flexibility in setting the range of motion limitations. For example, the controller 1002 can be programmed to allow for a greater range of motion during the time of day that a user has therapy, and a limited range of motion during the time of day that the user exercises.

In the illustrated embodiment, a load cell 1040 is operatively coupled to the controller 1002. The load cell 1040 can be used to trigger the controller 1002 to restrict rotation of one or both of the pistons 810 and 830 when the load cell 1040 is loaded. For example, the load cell 1040 can be placed in a shoe (not shown). In this particular embodiment, the load cell 1040 can trigger the controller 1002 to restrict rotation of the first and second pistons 810 and 830 when the shoe is subjected to a load. This embodiment could be useful, for example, for people who have lost the function of their quadriceps or have polio. In one embodiment, the load cell 1040 triggers the controller 1002 to restrict rotation of the first and second hinge members 910 and 920 at heal strike, allowing a person to put weight on the leg without concern of the knee bending. Once the toe is off the ground, the load cell 1040 triggers the controller 1002 to permit rotation of the first and second hinge members 910 and 920 so that the leg can be rotated forward. In other embodiments, the load cell 1040 can be positioned proximate to a muscle in the body. Accordingly, the tension of the muscle can trigger the load cell 1040 to allow or restrict rotation of the hinge members 910 and 920. In additional embodiments, the load cell 1040 can be positioned in other locations.

FIG. 12 is a front view of a knee brace 1260 having a bladder 1200 positioned to exert a force on the tibial tuberosity in accordance with one embodiment of the invention. The knee brace 1260 is similar to the knee brace 60 described above, and like reference numbers refer to like components in FIGS. 1–18. The knee brace 1260 of the illustrated embodiment can be used with the embodiments of the hinges 10 and 710 described above, and also with other types of single axis or bicentric hinges. Furthermore, the knee brace 1260 of the illustrated embodiment can be used with the embodiments of the power packs 800 and 1000 described above, and also with other types of power packs. In the illustrated embodiment, the bladder 1200 is positioned proximate to an inside surface 1422 (FIG. 14) of the lower frame 32. A fluid conduit 1220 couples the bladder 1200 to the power pack 800. The fluid conduit 1220 extends along an outside surface 1222 of the lower frame 32. In one embodiment, the fluid conduit 1220 can be disposed within a groove in the lower frame 32. In other embodiments, the fluid conduit 1220 can be disposed within the lower frame 32, or proximate to the inside surface 1422 of the lower frame 32. In the illustrated embodiment, the power pack 800 forces fluid through the fluid conduit 1220 to fill and drain the bladder 1200.

FIG. 13 is a partial cross-sectional view taken substantially along line 13—13 of FIG. 12. FIG. 13 illustrates the position of the bladder 1200 proximate to the tibial tuberosity of the leg (shown in broken lines). FIGS. 14A and 14B are partial cross-sectional views illustrating the bladder 1200 empty (FIG. 14A) and filled with fluid (FIG. 14B). Referring to FIGS. 13, 14A and 14B together, the bladder 1200 is positioned against a concaved backplate 1320 in an upper portion 1300 of the lower frame 32 in the illustrated embodiment. The concaved backplate 1320 has a rigid surface that forces the bladder 1200 to expand toward the tibial tuberosity when the bladder 1200 fills with fluid. The concaved backplate 1320 has an aperture 1310 to permit the fluid conduit 1220 to connect to the bladder 1200. The fluid conduit 1220 delivers fluid to the bladder 1200 through a fluid inlet/outlet 1400. In additional embodiments, the fluid conduit 1220 can connect the bladder 1200 to both the power packs 800 (FIG. 12) located on each side of the knee brace 1260 (FIG. 12). In the illustrated embodiment, when the hinge 10 is in the full-extension position (shown in FIG. 13), the bladder is expanded and filled with fluid (shown in FIGS. 13 and 14B) and accordingly exerts a force against the tibial tuberosity. When the hinge 710 is in the full-flexion position (shown in FIG. 7C), the bladder is empty (shown in FIG. 14A), and accordingly does not exert a force on the tibial tuberosity. One advantage of the embodiment illustrated in FIGS. 12–14 is that the knee brace 1260 provides a concentrated, dynamic counter-anterior instability force when the ACL needs support the most—at the point of full-extension. During flexion, when the ACL is under its lowest loads, the force is removed and the knee brace 1260 follows the knee motion in a comfortable manner.

Figure 15:
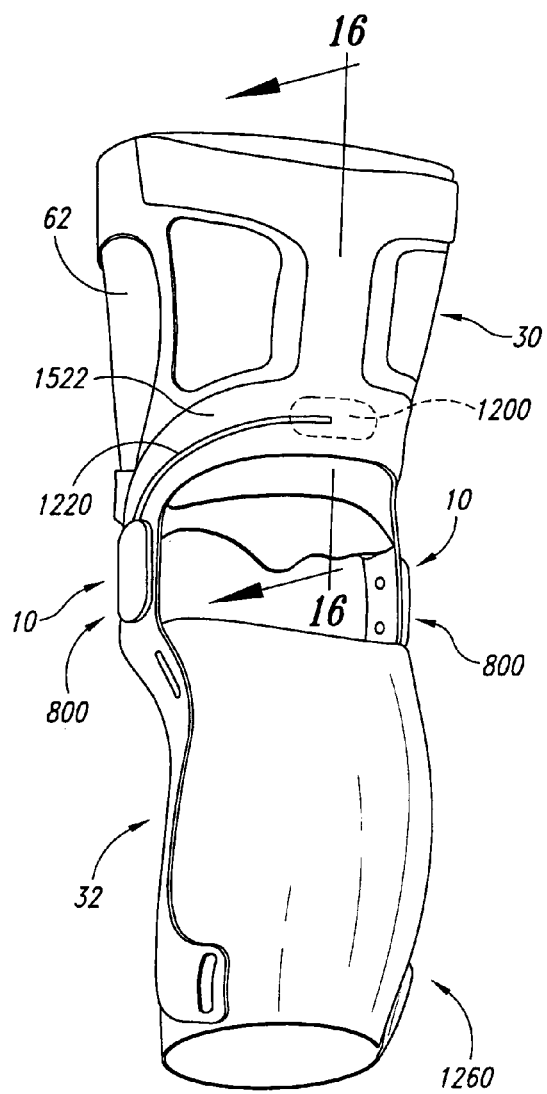
FIG. 15 is a rear isometric view of the knee brace with the bladder positioned to exert a posterior force on the femur in accordance with one embodiment of the invention.

FIG. 15 is a rear isometric view of the knee brace 1260 with the bladder 1200 positioned to exert a posterior force on the femur in accordance with another embodiment of the invention. In the illustrated embodiment, the bladder 1200 is positioned proximate to an inside surface 1622 (FIG. 16) of the upper frame 30. The fluid conduit 1220 couples the bladder 1200 to the power pack 800. The fluid conduit 1220 extends along an outside surface 1522 of the upper frame 30. In one embodiment, the fluid conduit 1220 can be disposed within a groove in the upper frame 30. In other embodiments, the fluid conduit 1220 can be disposed within the upper frame 30, or proximate to the inside surface 1622 of the upper frame 30. In the illustrated embodiment, the power pack 800 forces fluid through the fluid conduit 1220 to fill and drain the bladder 1200.

Figure 16:
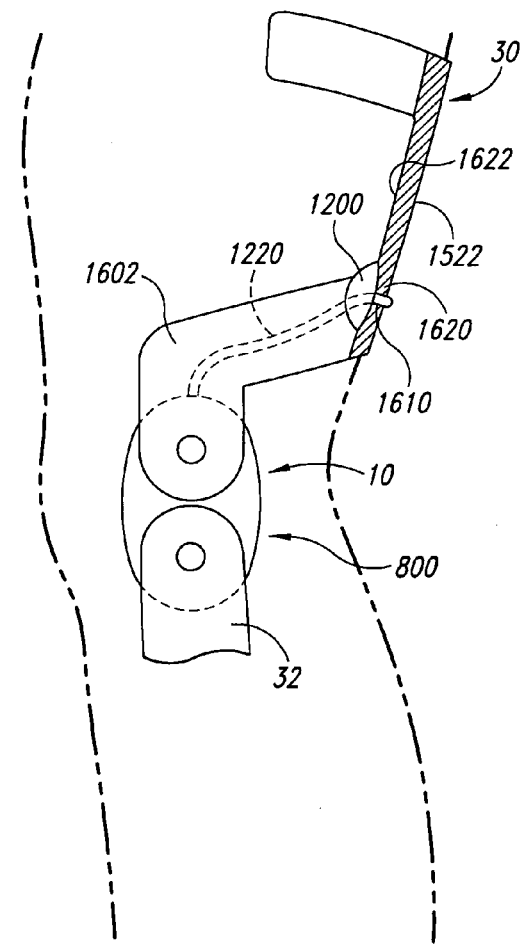
FIG. 16 is a partial cross-sectional view taken substantially along line 16—16 of FIG. 15.

FIG. 16 is a partial cross-sectional view taken substantially along line 16—16 of FIG. 15. FIG. 16 illustrates the position of the bladder 1200 proximate to the femur in the leg (shown in broken lines). The bladder 1200 is positioned against a concaved backplate 1620 in a lower portion 1602 of the upper frame 30 in the illustrated embodiment. The concaved backplate 1620 has a rigid surface that forces the bladder 1200 to expand toward the femur when the bladder 1200 fills with fluid. The concaved backplate 1620 has an aperture 1610 to permit the fluid conduit 1220 to connect to the bladder 1200. In additional embodiments, the fluid conduit can connect the bladder 1200 to both the power packs 800 (FIG. 15) located on each side of the knee brace 1260 (FIG. 15). In the illustrated embodiment, when the hinge 10 is in the full-extension position, the bladder is expanded and filled with fluid, and accordingly exerts a force against the femur. When the hinge 710 is in the full-flexion position (shown in FIG. 7C), the bladder is empty (shown in FIG. 14A) and accordingly does not exert a force on the femur. In additional embodiments, the knee brace can have a bladder positioned to exert a force on the femur and another bladder positioned to exert a force on the tibial tuberosity, or the knee brace can include only one of the bladders. One advantage of the embodiment illustrated in FIGS. 15 and 16 is that the knee brace 1260 provides a concentrated, dynamic counter-hyperextension posterior force when the PCL needs support the most, at full-extension. During flexion, the point where the PCL is under its lowest loads, the force is removed and the knee brace 1260 follows the knee motion in a comfortable manner.

Figure 17:
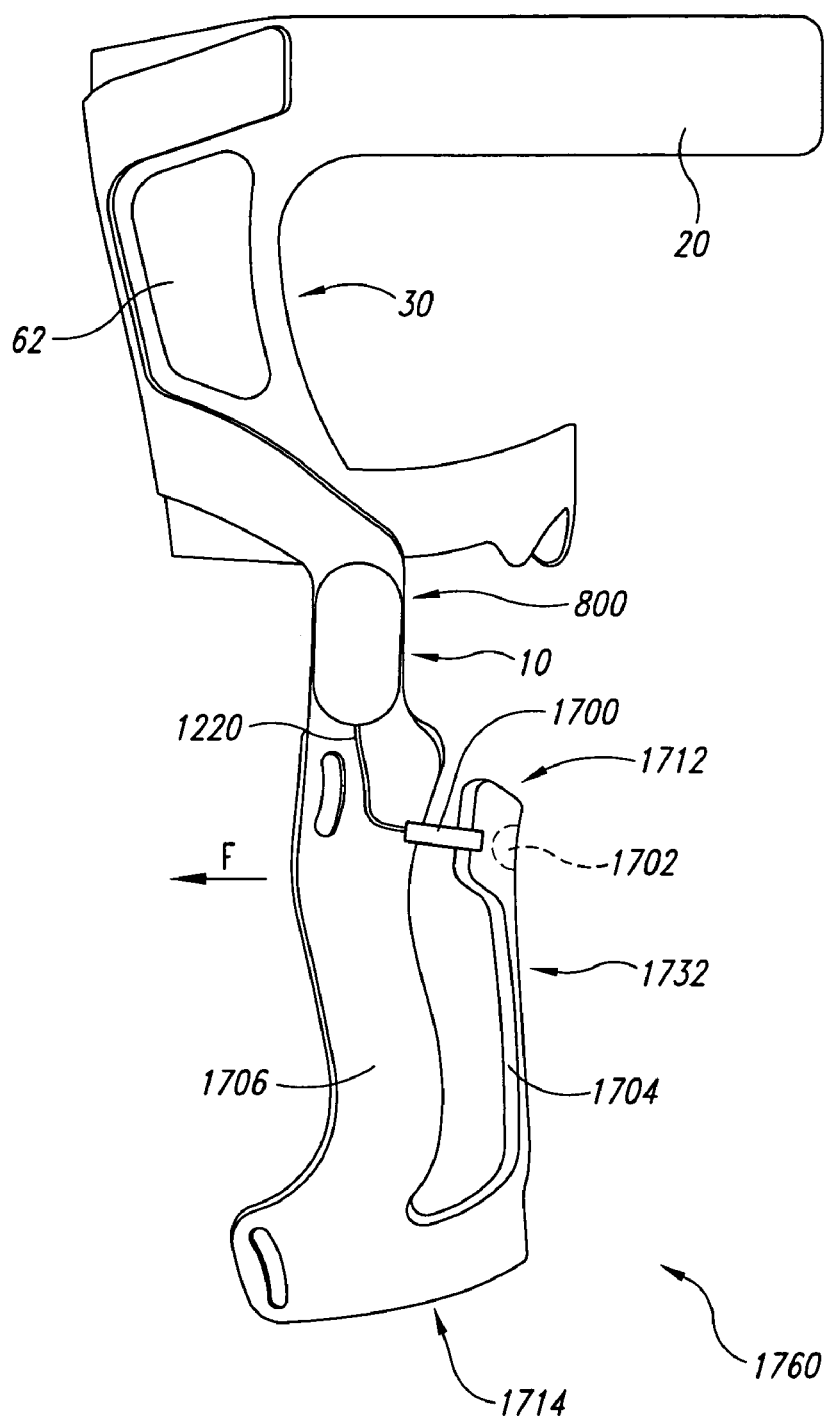
FIG. 17 is a side view of a knee brace with a lower frame having a front portion and a rear portion connected by a strap in accordance with another embodiment of the invention.
Figure 18A:
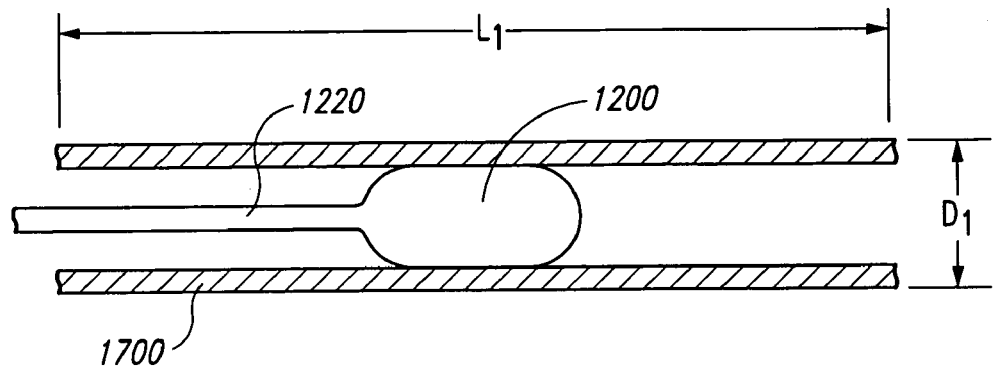
FIGS. 18A and 18B are partial side cross-sectional views illustrating the strap in the elongated and contracted positions.
Figure 18B:
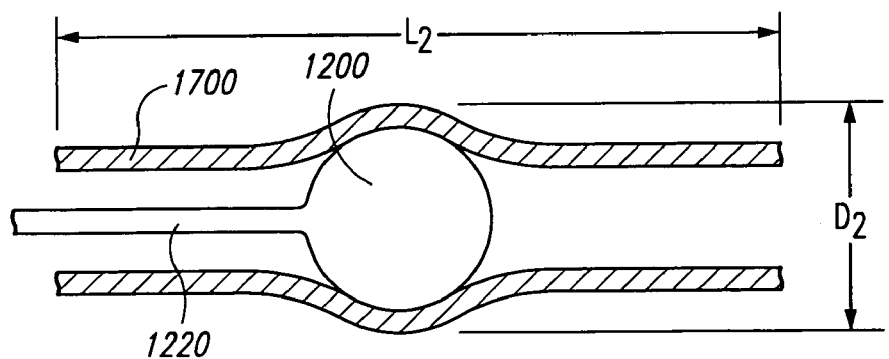

FIG. 17 is a side view of a knee brace 1760 with a lower frame 1732 having a front portion 1704 and a rear portion 1706 connected by a strap 1700 at a proximal end 1712 in accordance with another embodiment of the invention. The front portion 1704 of the lower frame 32 has a projection 1702 proximate to the proximal end 1712 of the front portion 1704. The strap 1700 is configured to selectively contract so that the proximal end 1712 of the front portion 1704 moves in the direction F. FIGS. 18A and 18B are partial side cross-sectional views illustrating the strap 1700 in the elongated (FIG. 18A) and contracted (FIG. 18B) positions. In the illustrated embodiment, the bladder 1200 is positioned inside the strap 1700 and is connected to the power pack 800 (FIG. 17) by the fluid conduit 1220. FIG. 18A illustrates the elongated position in which the strap 1700 has a diameter of $D_1$ and a length of $L_1$. FIG. 18B illustrates the strap 1700 after the bladder 1200 has filled with fluid. The expansion of the bladder 1200 causes a portion the strap 1700 proximate to the bladder 1200 to expand radially to a diameter $D_2$. The radial expansion of the strap 1700 proximate the bladder 1200 causes the length of the strap 1700 to decrease to $L_2$. Referring to FIG. 17, the contraction in the length of the strap 1700 causes the front portion 1704 to move in the direction F when the bladder 1200 is filled. The movement in the direction F causes the projection 1702 to exert a concentrated, dynamic force on the tibial tuberosity. As described above, the bladder 1200 is filled with fluid when the hinge 10 is in the full-extension position and the bladder 1200 is empty when the hinge 10 is in the full-flexion position.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

I claim:

1. A brace with a bladder for use in exerting a force on a limb, the brace comprising:
    a plate;
    a first frame member pivotally coupled to the plate, the first frame member being pivotable about a first axis of rotation;
    a second frame member pivotally coupled to the plate, the second frame member being pivotable about a second axis of rotation;
    a power pack, including:
        a housing having a cavity and an attachment mechanism configured to attach the housing to at least one of the plate, the first frame member, or the second frame member; and
        a piston disposed at least partially within the cavity, the piston having a head and an arm coupled to the head, the head being moveable in the cavity; and
    a bladder in fluid communication with the power pack so that the bladder expands as the piston displaces fluid, the bladder being positionable proximate to the limb, wherein the expansion of the bladder causes a force to be exerted on the limb.

2. The brace of claim 1 wherein the first axis of rotation and the second axis of rotation are the same.

3. The brace of claim 1 wherein at least one of the first or second frame members includes a recess for receiving the bladder.

4. The brace of claim 1 wherein the limb is a leg, the first frame member is positionable proximate to the upper leg, the second frame member is positionable proximate to the lower leg, the second frame member includes a recess for receiving the bladder, and the recess is positionable proximate to the tibial tuberosity in the leg.

5. The brace of claim 1 wherein the limb is a leg, the first frame member is positionable proximate to the upper leg, the second frame member is positionable proximate to the lower leg, the first frame member includes a recess for receiving the bladder, and the recess is positionable proximate to the femur in the leg.

6. A brace for applying a force on a limb, the brace comprising:
    an upper frame;
    a lower frame;
    a hinge coupling the upper frame to the lower frame, the upper frame being moveable relative to the lower frame;
    a hydraulic pump coupled to at least one of the hinge, the upper frame, or the lower frame, the hydraulic pump being configured to generate a fluid flow; and
    a bladder coupled to the hydraulic pump, the bladder positioned to expand as it receives the fluid flow and apply a force to the limb;
    wherein the hydraulic pump is configured to generate the fluid flow when at least one of the upper or lower frame moves relative to the other.

7. The brace of claim 6 wherein at least one of the upper or lower frame includes a recess for receiving the bladder.

8. The brace of claim 6 wherein the limb is a leg, the upper frame is positionable proximate to the upper leg, the lower frame is positionable proximate to the lower leg, the lower frame includes a recess for receiving the bladder, and the recess is positionable proximate to the tibial tuberosity in the leg.

9. The brace of claim 6 wherein the limb is a leg, the upper frame is positionable proximate to the upper leg, the lower frame is positionable proximate to the lower leg, the upper frame includes a recess for receiving the bladder, and the recess is positionable proximate to the femur in the leg.

10. The brace of claim 6, further comprising a fluid conduit for coupling the hydraulic pump to the bladder.

11. A knee brace for applying a dynamic force proximate to the knee joint, the brace comprising:
    a hinge;
    an upper frame pivotally coupled to the hinge, the upper frame being pivotable about a first axis of rotation;
    a lower frame pivotally coupled to the hinge, the lower frame being pivotable about a second axis of rotation;
    a hydraulic pump coupled to the hinge, the hydraulic pump being configured to generate a fluid flow as the upper frame pivots about the first axis of rotation and/or the lower frame pivots about the second axis of rotation; and a bladder positioned proximate to the upper frame or the lower frame, the bladder being in fluid communication with the hydraulic pump to receive the fluid flow and expand to exert a force against the knee joint.

12. The brace of claim 11 wherein at least one of the upper or lower frame includes a recess for receiving the bladder.

13. The brace of claim 11 wherein the upper frame is positionable proximate to an upper leg, the lower frame is positionable proximate to a lower leg, the lower frame includes a recess for receiving the bladder, and the recess is positionable proximate to the tibial tuberosity.

14. The brace of claim 11 wherein the upper frame is positionable proximate to an upper leg, the lower frame is positionable proximate to a lower leg, the upper frame includes a recess for receiving the bladder, and the recess is positionable proximate to the femur.

15. The brace of claim 11, further comprising a fluid conduit for coupling the hydraulic pump to the bladder.

16. A knee brace for applying a force on a limb, the brace comprising:
   a hinge;
   a first brace portion having a projection for applying the force on the limb;
   a second brace portion coupled to the first brace portion and the hinge;
   a strap having a first end attached to the first brace portion and a second end attached to the second brace portion;
   a hydraulic pump coupled to the hinge, the first brace portion or the second brace portion, the hydraulic pump generating a fluid flow;
   a bladder disposed within the strap being in fluid communication with the hydraulic pump to receive the fluid flow and expand, the expansion of the bladder causing the strap to expand radially, wherein the radial expansion of the strap moves the first brace portion toward the second brace portion and the limb so that the projection applies the force to the limb.

17. The brace of claim 16, wherein the limb is a leg and the projection is positionable proximate to the tibial tuberosity in the leg.

18. The brace of claim 16, further comprising a fluid conduit for coupling the hydraulic pump to the bladder.

19. The brace of claim 16 wherein the strap is extensible between a first length and a second length.

* * * * *